US009212189B2

(12) United States Patent
Chang et al.

(10) Patent No.: US 9,212,189 B2
(45) Date of Patent: Dec. 15, 2015

(54) FLUORESCENT PROBES FOR REACTIVE SULFUR SPECIES

(75) Inventors: Christopher J. Chang, Berkeley, CA (US); Alexander R. Lippert, Dallas, TX (US); Vivian S. Lin, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 494 days.

(21) Appl. No.: 13/493,253

(22) Filed: Jun. 11, 2012

(65) Prior Publication Data
US 2012/0329085 A1 Dec. 27, 2012

Related U.S. Application Data

(60) Provisional application No. 61/495,779, filed on Jun. 10, 2011.

(51) Int. Cl.
*C12Q 1/02* (2006.01)
*C07D 493/10* (2006.01)
*C12Q 1/00* (2006.01)
*G01N 21/64* (2006.01)

(52) U.S. Cl.
CPC ............... *C07D 493/10* (2013.01); *C12Q 1/00* (2013.01); *G01N 21/64* (2013.01)

(58) Field of Classification Search
CPC .... A01B 12/006; C07D 493/10; G01N 21/64; C12Q 1/00
See application file for complete search history.

(56) References Cited

U.S. PATENT DOCUMENTS

2008/0241856 A1* 10/2008 Wong et al. .................... 435/7.1
2010/0190159 A1* 7/2010 Abe et al. ......................... 435/6

OTHER PUBLICATIONS

Novikova et al. Polimery (2001) 46(6): 406-413, abstract only downloaded from CAPLUS Nov. 2, 2014.*
Abe K. and Kimura, H., "The Possible Role of Hydrogen Sulfide as an Endogenous Neuromodulator", *The Journal of Neuroscience*, vol. 16, No. 3, pp. 1066-1071, 1996.
Blackstone, E. et al., "H$_2$S Induces a Suspended Animation-Like State in Mice", *Science*, vol. 308, No. 5721, p. 518, 2005.
Choi, M.G. et al., "Sulfide-selective chemosignaling by a Cu$^{2+}$ complex of dipicolylamine appended fluorescein", *Chem. Commun.*, Issue 47, pp. 7390-7392, 2009.
Choi, M.M.F., "Fluorometric Optode Membrane for Sulfide Detection", *Analyst* (London. 1877. Print), 123(7), pp. 1631-1634, 1998.
Estrela, J.M. et al., "Glutathione in Cancer Biology and Therapy", *Critical Reviews in Clinical Laboratory Sciences*, vol. 43, No. 2 , pp. 143-181, 2006.
Eto K. et al., "Brain hydrogen sulfide is severely decreased in Alzheimer's disease", *Biochemical and Biophysical Research Communications*, vol. 293, No. 5, pp. 1485-1488, 2002.
Fiorucci, S. et al., "The third gas: H$_2$S regulates perfusion pressure in both the isolated and perfused normal rat liver and in cirrhosis", *Hepatology*, vol. 42, No. 3, pp. 539-548, 2005.
Furne, J. et al., "Whole tissue hydrogen sulfide concentrations are orders of magnitude lower than presently accepted values", *Am J Physiol Regul Integr Comp Physiol*, vol. 295, pp. R1479-R1485, 2008.
Garrett, R.M. et al., "Human sulfite oxidase R160Q: Identification of the mutation in a sulfite oxidase-deficient patient and expression and characterization of the mutant enzyme", *Proc Natl Acad Sci U S A.*, vol. 95, pp. 6394-6398, 1998.
Han, Y. et al., "Hydrogen sulfide and carbon monoxide are in synergy with each other in the pathogenesis of recurrent ferbrile seizures", *Cell. Mol. Neurobiol.*, vol. 26, No. 1, pp. 101-107, 2006.
Ishigami, M. et al., "A Source of Hydrogen Sulfide and a Mechanism of Its Release in the Brain", *Antioxidants and Redox Signaling*, vol. 11, No. 2, 2009.
Kabil, O. and Banjaree, R., "Redox Biochemistry of Hydrogen Sulfide", *Journal of Biological Chem.*, vol. 285, pp. 21903-21907, 2010.
Kamoun, P. et al., "Endogenous hydrogen sulfide overproduction in Down syndrome", *American Journal of Medical Genetics*, vol. 116A, No. 3, pp. 310-311, 2003.
Lawerence, N. et al., "The Electrochemical Analog of the Methylene Blue Reaction: A Novel Amperometric Approach to the Detection of Hydrogen Sulfide", *Electroanalysis*, vol. 12, No. 18, pp. 1453-1460, 2000.
Li, L. et al., "Hydrogen Sulfide and Cell Signaling", *Annual Review of Pharmacology and Toxicology*, vol. 51: pp. 169-187, 2011.
Li, L. et al., "Hydrogen sulfide is a novel mediator of lipopolysaccharide-induced inflammation in the mouse", *FASEB*, vol. 19, No. 9, 2005.
Mustafa, A.K. et al., "H$_2$S Signals Through Protein S-Sulfhydration", *Sci Signal*, vol. 2, No. 96, 2009.
Nicholson, C. and Calvert, J., "Hydrogen Sulfide and Ischemia-Reperfusion Injury", *Pharmacol Res.*, vol. 62, No. 4, pp. 289-297, 2010.
Papapetropoulos, A. et al., "Hydrogen sulfide is an endogenous stimulator of angiogenesis", *PNAS*, vol. 106, No. 51, pp. 21972-21977, 2009.
Paulsen, C.E. and Carroll, K.S., "Orchestrating Redox Signaling Networks through Regulatory Cysteine Switches", *ACS Chem. Biol.*, vol. 5, No. 1 pp. 47-62, 2010.
Peng, Y. et al., "H$_2$S mediates O$_2$ sensing in the carotid body", *PNAS*, vol. 107, No. 23, pp. 10719-10724, 2010.
Seth, D. and Stamler, J. S., "The SNO-proteome: Causation and Classifications", *Curr. Opin. Chem. Biol.*, vol. 15, No. 1, pp. 129-136, 2011.
Sies, H., "Glutathione and its role in cellular functions", *Free Radical Biology and Medicine*, vol. 27, Issue 9, pp. 916-921, 1999.
Warenycia, M. W. et al., "Acute Hydrogen Sulfide Poisoning. Demonstration of Selective Uptake of Sulfide by the Brainstem by Measurement of Brain Sulfide Levels." *Biochem. Pharmacol.*, vol. 38, No. 6, pp. 973-981, 1989.

(Continued)

Primary Examiner — Susan Hanley
(74) Attorney, Agent, or Firm — Morgan, Lewis & Bockius LLP; Jeffry S. Mann

(57) ABSTRACT

The invention provides reaction-based fluorescent probes for selective imaging of hydrogen sulfide in living cells.

17 Claims, 15 Drawing Sheets

(56) References Cited

OTHER PUBLICATIONS

Yang, G. et al., "H$_2$S as a Physiologic Vasorelaxant: Hypertension in Mice with Deletion of Cystathionine γ-Lyase", *Science*, vol. 322, No. 5901, pp. 587-590, 2008.

Yang, G. et al., "Pro-apoptotic effect of endogenous H$_2$S on human aorta smooth muscle cells", *FASEB*, vol. 20, No. 3, 2006.

Yang, W. et al., "Activation of K$_{ATP}$ channels by H$_2$S in rat insulin-secreting cells and the underlying mechanisms", *J Physiol*, vol. 569, pp. 519-531, 2005.

\* cited by examiner

FIG. 5
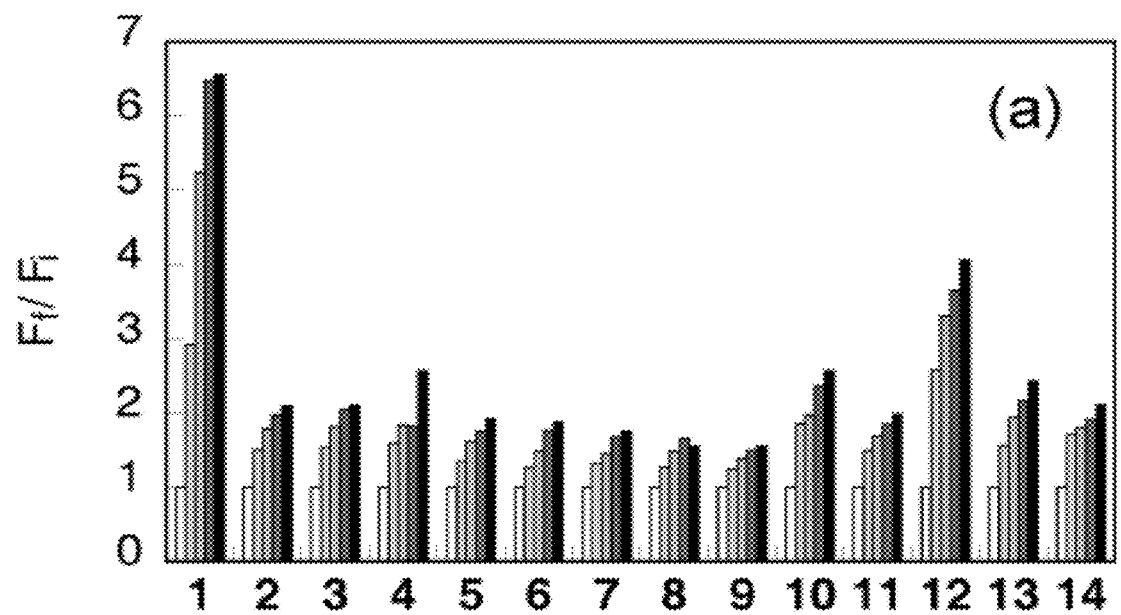
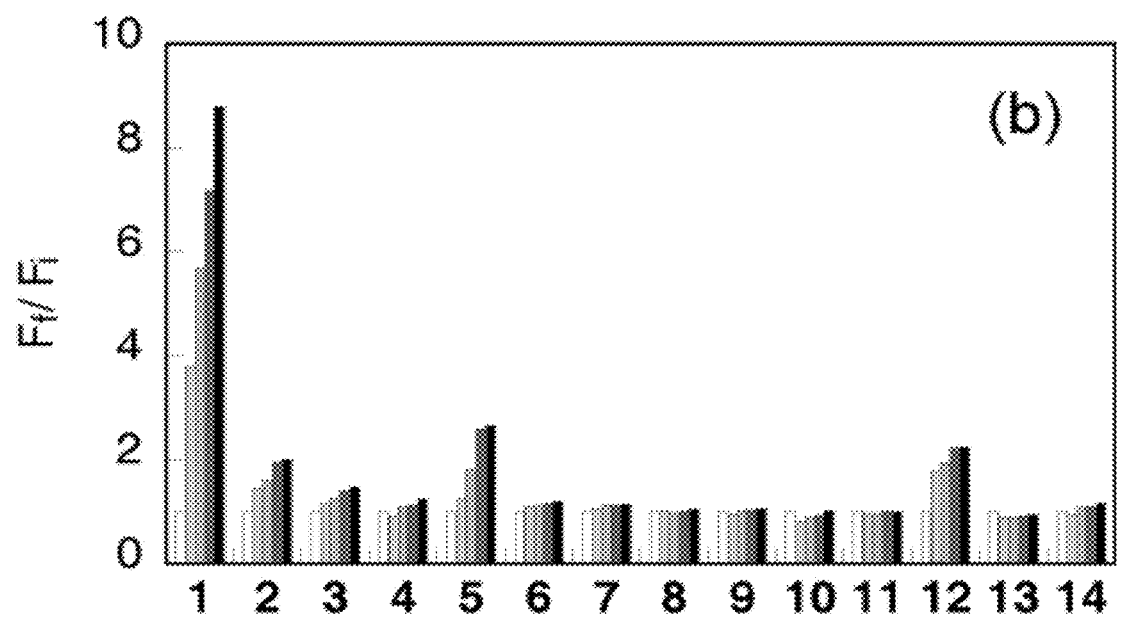

FIG. 7
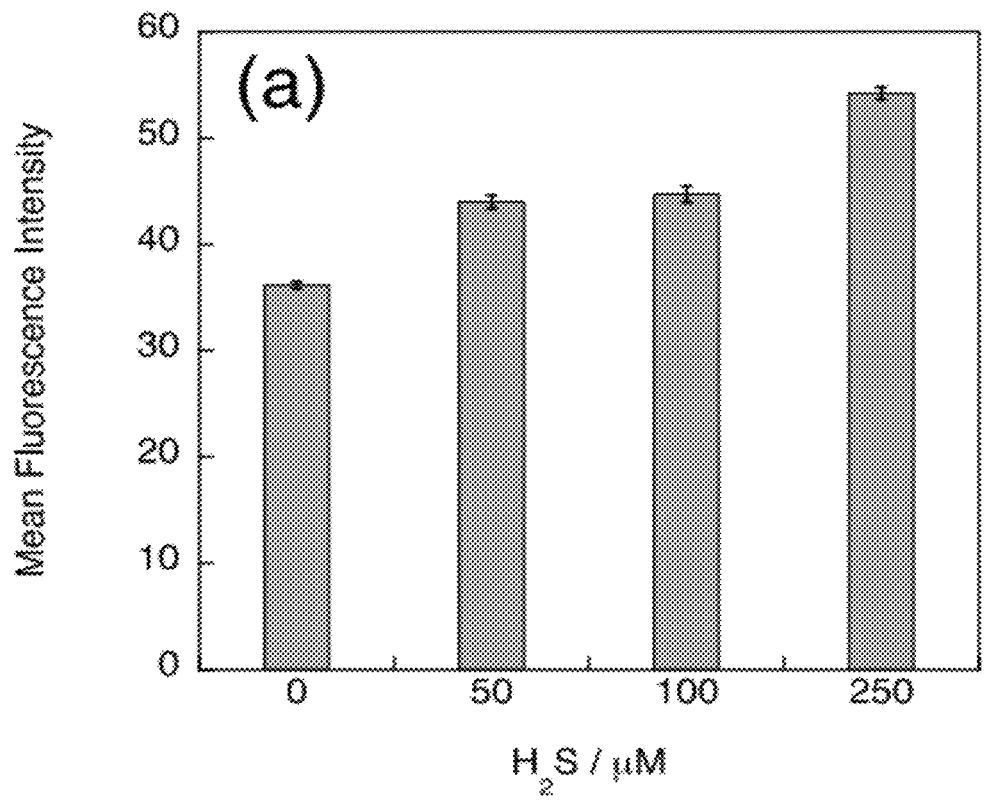
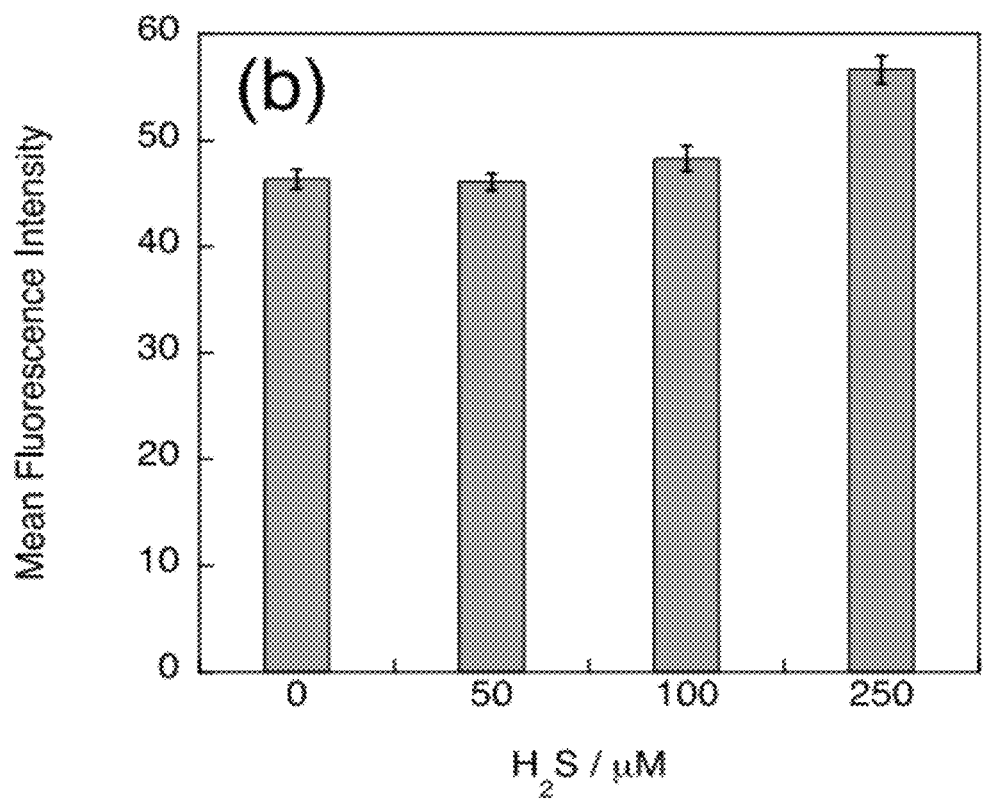

FLUORESCENT PROBES FOR REACTIVE SULFUR SPECIES

CROSS-REFERENCE TO RELATED APPLICATIONS

This application claims priority under 35 U.S.C. §119(e) to U.S. Provisional Patent Application No. 61/495,779, filed on Jun. 10, 2011, the disclosure of which is incorporated herein by reference in its entirety for all purposes.

STATEMENT OF GOVERNMENT SUPPORT

This invention was made with Government support under Grant No. GM 079465, awarded by the National Institutes of Health. The Government has certain rights in the invention.

BACKGROUND OF THE INVENTION $H_2S$ is emerging as an important mediator of human physiology and pathology, but remains difficult to study due to the lack of methods to detect this gaseous signaling molecule in living systems in real time. $H_2S$ is a member of a family of endogenously produced reactive sulfur species (RSS) that includes thiols,[i,ii] S-nitrosothiols,[iii] sulfenic acids,[iv] and sulfite,[v] and plays vital roles in the regulation of intracellular redox states,[vi] as well as other fundamental signaling pathways involved in human health and disease.[vii] Like other gaseous signaling molecules nitric oxide (NO) and carbon monoxide (CO), $H_2S$ can interact directly with proteins, both by post-translationally modifying cysteine residues via sulfhydration,[viii] as well as by binding to the iron center in heme groups.[ix] $H_2S$ is important in many physiological processes including vasodilation,[x] angiogenesis,[xi] oxygen sensing,[xii] apoptosis,[xiii] inflammation,[xiv] and neuromodulation,[xv] and can protect against ischemia/reperfusion injury.[xvi] Furthermore, $H_2S$ levels are altered in a number of disease states including Alzheimer's disease,[xvii] Down's syndrome,[xviii] diabetes,[xix] and cirrhosis of the liver.[xx] Given this dichotomy between health and pathology, new methods to directly monitor the production and trafficking of $H_2S$ in living systems are urgently needed and would contribute to a deeper understanding of the role this species plays in human biology.

Current methods for $H_2S$ detection including colorimetric assays,[xxi,xxii,xxiii] electrochemical detection,[xxiv] gas chromatography techniques,[xxv] and metal-induced precipitation of sulfide,[xxvi] depend acutely on the precise procedures used for the processing of tissues or cell lysates and yield variable estimates of endogenous $H_2S$ that range from nM to high $\mu M$.[xxv,xxvii,xxviii] Our invention provides a general solution to this and other problems.

SUMMARY OF INVENTION

The present invention provides numerous fluorescent probes and methods of their use. In an exemplary embodiment, the invention provides reaction-based fluorescent probes for selective imaging of hydrogen sulfide in living cells. The methods provide a unique solution to the problem of detecting and imaging of $H_2S$ in living, intact systems.

One key advantage of various embodiments of the invention is that they can be used to detect $H_2S$ in living, intact cells with no additional processing. This allows for a much more accurate and relevant measure of endogenous $H_2S$ levels. Additionally, these probes have the advantages of: 1. The detection of $H_2S$ with spatiotemporal resolution; 2. Selectivity for $H_2S$ over other biologically relevant ROS, RNS, and RSS; 3. Low toxicity; 4. Ease of use; 5. Tunability of color and dynamic range. Taken together, these qualities endow our invention with great potential for biochemical and biomedical research and clinical and drug-development assays. Compared to post-mortem cellular processing, the real-time detection can be used to directly assay $H_2S$ levels in intact system, providing a more accurate and relevant measure of $H_2S$ levels. The tunability of the colors and reactivities of these probes could be uniquely useful to provide multicolor array strips to provide rapid $H_2S$ quantitation in field samples.

BRIEF DESCRIPTION OF THE DRAWINGS

FIG. 5. Fluorescence responses of (a) 10 μM SF1 and (b) 10 μM SF2 to biologically relevant RSS, RNS, and ROS. Bars represent relative responses at 525 nm at 0, 15, 30, 45, and 60 min after addition of RSS, RNS, or ROS. Data shown are for 5 mM glutathione, 5 mM cysteine, and 100 μM for other RSS, RNS, and ROS. Data were acquired in 20 mM HEPES buffered at pH 7.4 with excitation at $\lambda_{ex}$=488 nm. 1. $H_2S$; 2. glutathione; 3. cysteine; 4. lipoic acid; 5. $Na_2SO_3$; 6. $NaS_2O_3$; 7. KSCN; 8. S-nitroso glutathione; 9. $NaNO_2$; 10. NO; 11. $H_2O_2$; 12. $O_2^-$; 13. 'BuOOH; 14. HOCl.

FIG. 7. Mean fluorescence intensity of confocal images of H2S detected in live HEK293T cells treated with 0, 50, 100, and 250 μM $H_2S$. (a) HEK293T cells were incubated with SF1 for 60 min at 37° C. with the indicated amount of $H_2S$ added for the final 30 min. (b) HEK293T cells were incubated with SF2 for 60 min at 37° C. with the indicated amount of $H_2S$ added for the final 30 min. Data represent the mean fluorescence intensity of distinct fields (n=4). Error bars are ±s.e.m.

DETAILED DESCRIPTION OF THE INVENTION

Definitions

Figure 1:
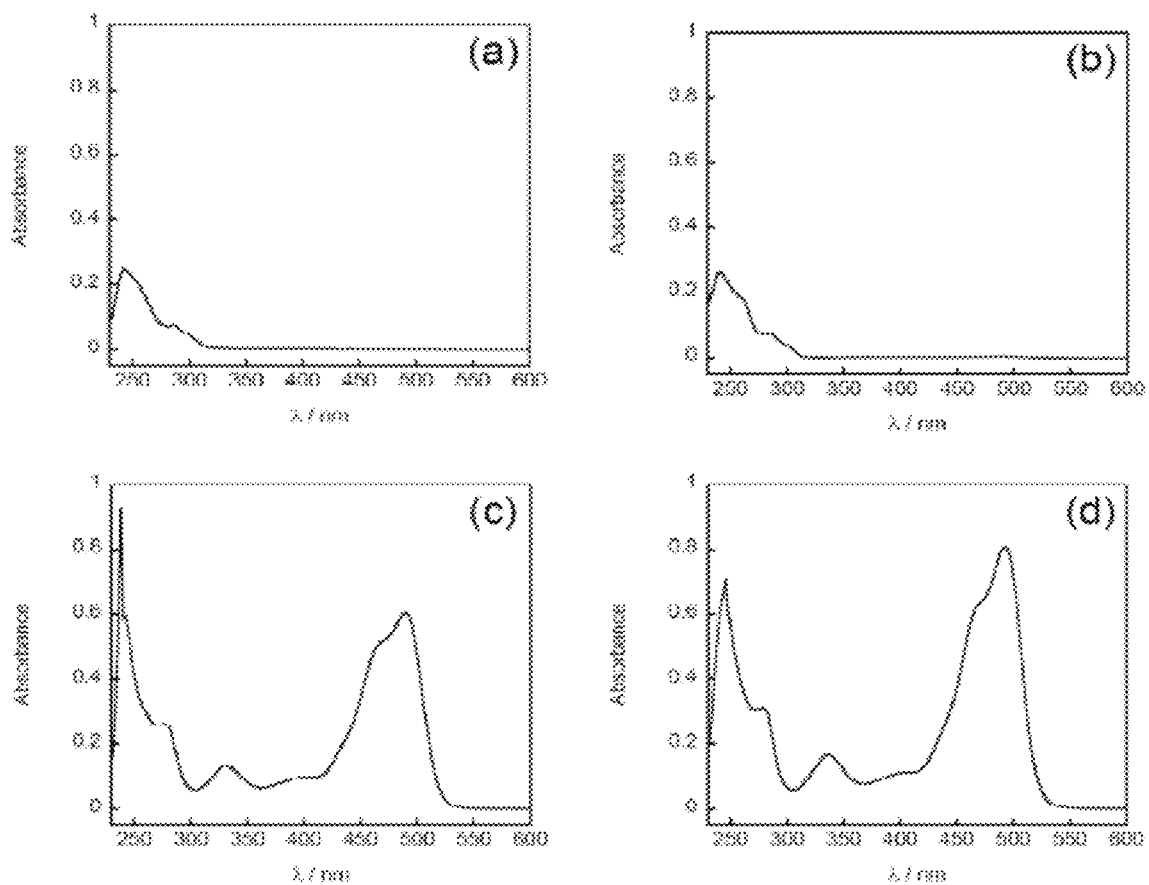
FIG. 1. Absorbance spectra of (a) 10 μM SF1 (b) 10 μM SF2, and 10 μM of rhodamine products (c) tert-butoxycarbonyl-rhodamine 110 and (d) morpholinourea-rhodamine 110.

The term "alkyl", by itself or as part of another substituent, means a straight or branched chain hydrocarbon radical, which may be fully saturated, mono- or polyunsaturated. For convenience, the term alkyl may refer to divalent (i.e., alkylene) and other multivalent radicals in addition to monovalent radicals. Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like. An unsaturated alkyl group is one having one or more double bonds or triple bonds (i.e., alkenyl and alkynyl moieties). Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

Typically, an alkyl (or alkylene) group will have from 1 to 30 carbon atoms, That is, in some embodiments, alkyl refers to an alkyl having a number of carbons selected from $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$ and any combination thereof. In some embodiments, alkyl refers to $C_1$-$C_{25}$ alkyl. In some embodiments, alkyl refers to $C_1$-$C_{20}$ alkyl. In some embodiments, alkyl refers to $C_1$-$C_{15}$ alkyl. In some embodiments, alkyl refers to $C_1$-$C_{10}$ alkyl. In some embodiments, alkyl refers to $C_1$-$C_6$ alkyl.

The term "heteroalkyl", by itself or in combination with another term, means an alkyl in which at least one carbon is replaced with an atom other than carbon (i.e., a heteroatom). In some embodiments, the heteroatom is selected from O, N and S, wherein the nitrogen and sulfur atoms may optionally be oxidized and the nitrogen heteroatom may optionally be quaternized. In some embodiments, a heteroalkyl is any $C_2$-$C_{30}$ alkyl, $C_2$-$C_{25}$ alkyl, $C_2$-$C_{20}$ alkyl, $C_2$-$C_{15}$ alkyl, $C_2$-$C_{10}$ alkyl or $C_2$-$C_6$ alkyl in any of which one or more carbons are replaced by one or more heteroatoms selected from O, N and S. The heteroatoms O, N and S may be placed at any interior position of the heteroalkyl group and may also be the position at which the heteroalkyl group is attached to the remainder of the molecule. In some embodiments, depending on whether a heteroatom terminates a chain or is in an interior position, the heteroatom may be bonded to one or more H or $C_1$, $C_2$, $C_3$, $C_4$, $C_5$ or $C_6$ alkyl according to the valence of the heteroatom. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$. The term "heteroalkylene" may be use to refer a divalent radical derived from heteroalkyl. Unless otherwise stated, no orientation of the linking group is implied by the direction in which a divalent group is written. For example, the formula —C(O)$_2$R'— represents both —C(O)$_2$R'— and —R'C(O)$_2$—.

The terms "cycloalkyl" and "heterocycloalkyl", by themselves or in combination with other terms refer to cyclic versions of "alkyl" and "heteroalkyl", respectively. For heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl and the like.

The terms "halo" or "halogen" refer to fluorine, chlorine, bromine and iodine. Additionally, terms such as "haloalkyl," are meant to include monohaloalkyl and polyhaloalkyl.

The term "aryl" refers to a polyunsaturated, aromatic hydrocarbon that can be a single ring or multiple rings (preferably 1, 2 or 3 rings) that are fused together or linked covalently. For convenience, the term aryl may refer to divalent (i.e., arylene) and other multivalent radicals in addition to monovalent radicals. In some embodiments, aryl is a 3, 4, 5, 6, 7 or 8 membered ring that is optionally fused to one or two other 3, 4, 5, 6, 7 or 8 membered rings.

The term "heteroaryl" refers to aryl containing 1, 2, 3 or 4 heteroatoms selected from N, O and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

In some embodiments, any alkyl, heteroalkyl, cycloalkyl, heterocycloalkyl, aryl and heteroaryl may be substituted. Preferred substituents for each type of radical are provided below.

Substituents for alkyl, heteroalkyl, cycloalkyl and heterocycloalkyl radicals (including those groups often referred to as alkylene, alkenyl, heteroalkylene, heteroalkenyl, alkynyl, cycloalkenyl, and heterocycloalkenyl) are generically referred to as "alkyl group substituents". In some embodiments, an alkyl group substituent is selected from —R', —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O) NR"R"', —NR"C(O)$_2$R', —NR—C(NR'R"R"')=NR"", —NR—C(NR'R")=NR"', —S(O)R', —S(O)$_2$R', —S(O)$_2$ NR'R", —NRSO$_2$R', —CN and —NO$_2$. Embodiments of R', R", R"' and R"" are provided below. Substituents for aryl and heteroaryl groups are generically referred to as "aryl group substituents". In some embodiments, an aryl group substituent is selected from —R', —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN, —NO$_2$ and —N$_3$. In some embodiments, R', R", R"' and R"" are each independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In some embodiments, R', R", R"' and R"" are each independently selected from hydrogen, unsubstituted alkyl, unsubstituted heteroalkyl, unsubstituted cycloalkyl, unsubstituted heterocycloalkyl, unsubstituted aryl and unsubstituted heteroaryl. In some embodiments, R', R", R' and R"" are each independently selected from hydrogen and unsubstituted alkyl (e.g., $C_1$, $C_2$, $C_3$, $C_4$, $C_5$ and $C_6$ alkyl).

Two substituents on adjacent atoms of an aryl or heteroaryl ring may optionally be replaced with a substituent of the formula -T-C(O)—(CRR')$_q$—U—, wherein T and U are independently selected from —NR—, —O—, —CRR'— and a single bond, and q is an integer selected from 0, 1, 2 and 3. Alternatively, two of the substituents on adjacent atoms of an aryl or heteroaryl ring may optionally be replaced with a substituent of the formula -A-(CH$_2$)$_r$—B—, wherein A and B are independently selected from CRR'—, —O—, —NR—, —S—, —S(O)—, —S(O)$_2$—, —S(O)$_2$NR'— and a single bond, and r is an integer selected from 1, 2, 3 and 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R"')$_d$—, where s and d are independently integers selected from 0, 1, 2 and 3, and X is selected from —O—, —NR'—, —S—, —S(O)—, —S(O)$_2$— and —S(O)$_2$NR'—. The substituents R, R', R" and R"' are preferably independently selected from hydrogen and substituted or unsubstituted ($C_1$-$C_6$)alkyl.

Unless otherwise specified, the symbol "R" is a general abbreviation that represents a substituent group that is selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound includes more than one R, R', R", R"' and R"" group, they are each independently selected.

For groups with exchangeable or acidic protons, the ionized form is equally contemplated. For example, —COOH also refers to —COO$^-$ while —SO$_3$H also refers to —SO$_3^-$.

The symbol ⁓, displayed perpendicular to a bond, or the symbol *, displayed at the end of a bond, indicates the point at which the displayed moiety is attached to the remainder of the molecule.

In some embodiments, the definition of terms used herein is according to IUPAC.

Introduction

Figure 2:
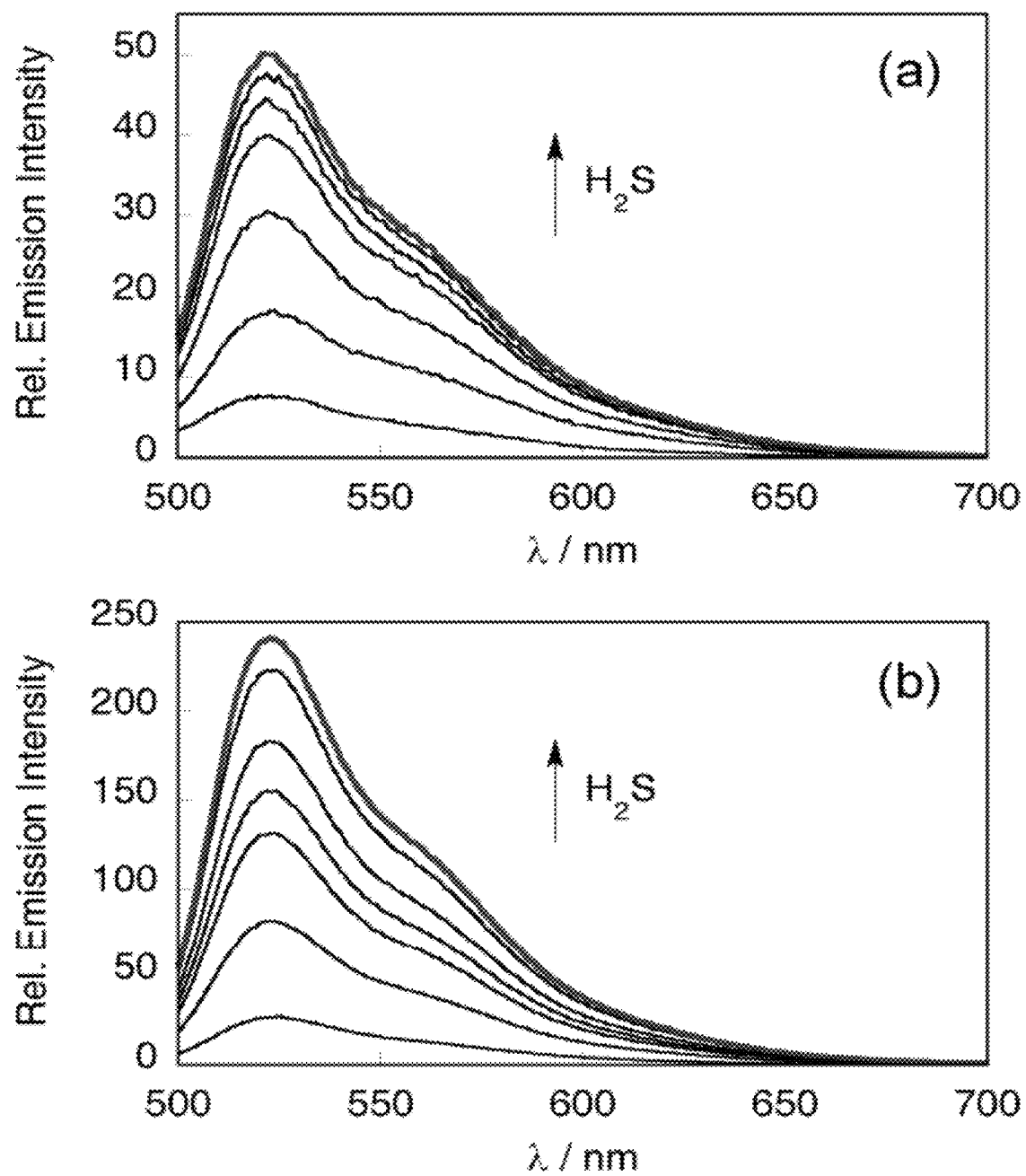
FIG. 2. Fluorescence responses of (a) 10 μM SF1 and (b) 10 μM SF2 to 100 μM $H_2S$. Data were acquired at 25° C. in 20 mM HEPES buffered to pH 7.4 with excitation at $\lambda_{ex}$=488 nm. Emission was collected between 498 and 700 nm. Time points represent 0, 10, 20, 30, 40, 50, and 60 min (red trace) after addition of 100 μM $H_2S$. Reactions are not complete at these time points.
Figure 3:
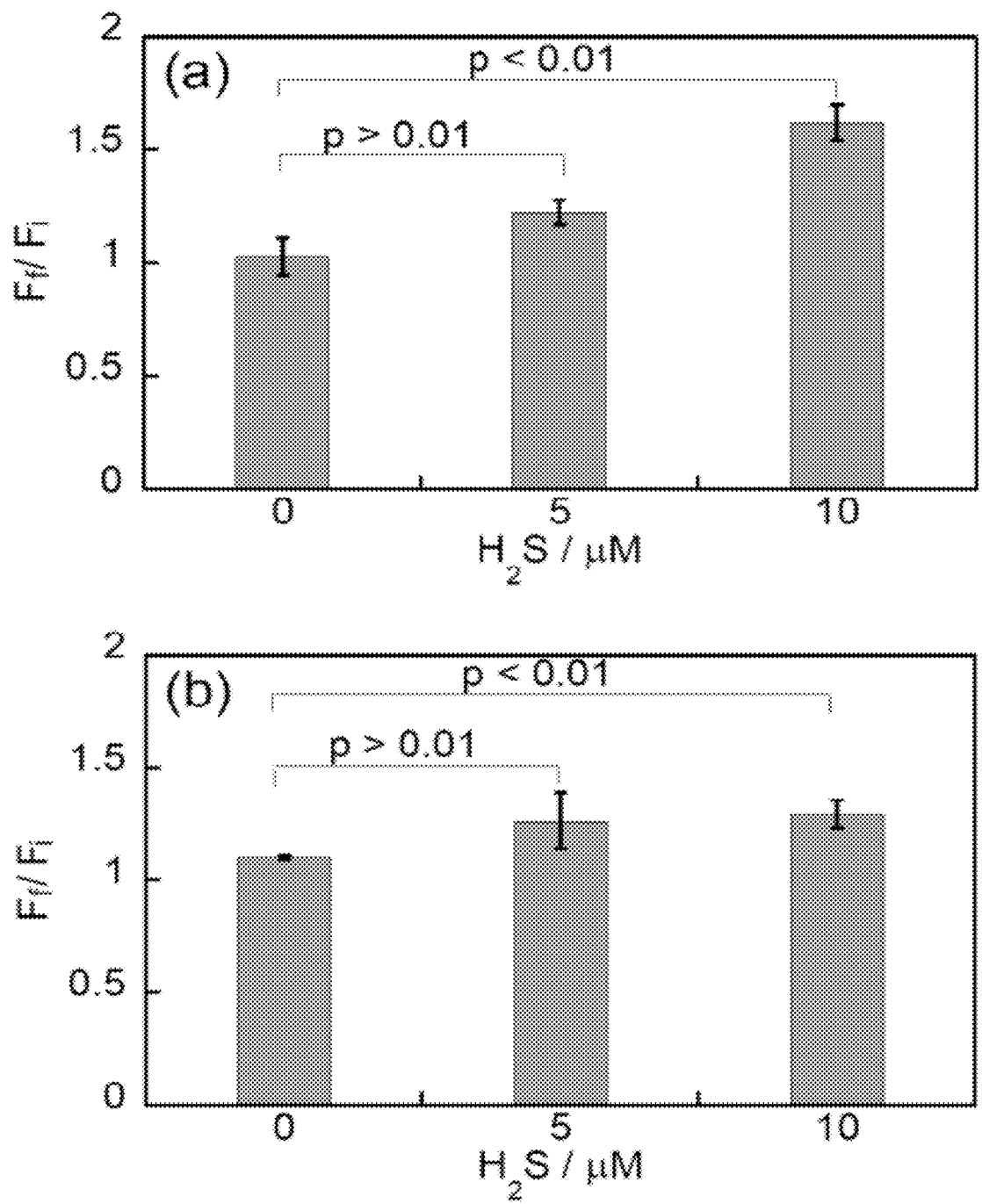
FIG. 3. Fluorescence responses of (a) 10 μM SF1 and (b) 10 μM SF2 to 0, 5, and 10 μM $H_2S$ after 60 min. Data were acquired at 25° C. in 20 mM HEPES buffered to pH 7.4 with excitation at $\lambda_{ex}$=488 nm. Statistical analyses were performed with a two-tailed Student's t-test (n=3). Error bars are ±standard deviation.
Figure 4:
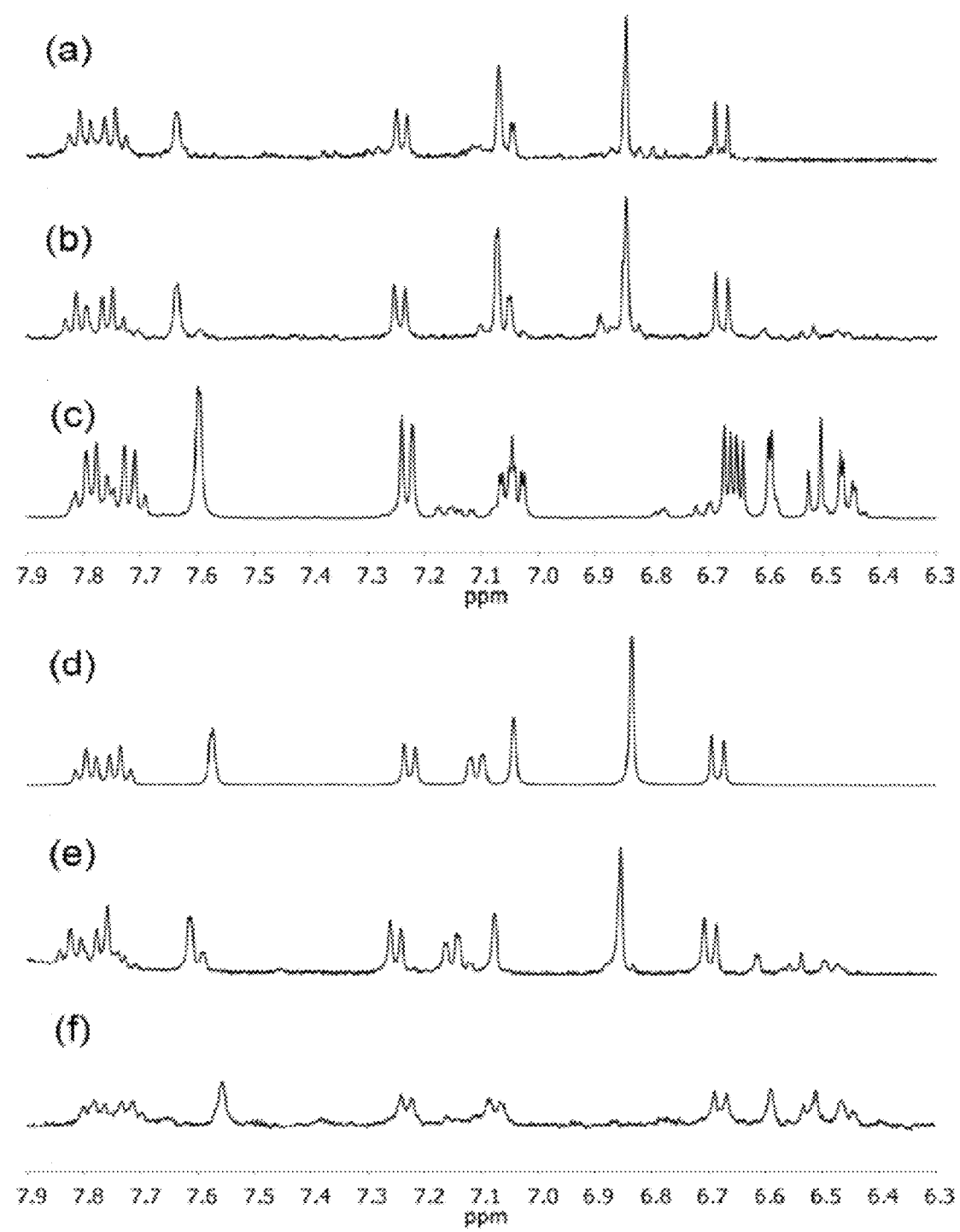
FIG. 4. 1H NMR (400 MHz, $CD_3OD$) spectra of (a) SF1, (b) the reaction of 500 μM SF1 with 10 mM NaSH, (c) tert-Butoxycarbonyl-rhodamine 110, (d) SF2, (e) the reaction of 500 μM SF2 with 10 mM NaSH, and (f) morpholinourea-rhodamine 110. Reactions are not complete at these early time points.

The general utility of our invention is the selective detection of H$_2$S in living cells using confocal or fluorescence microscopy. We designed azide-containing probes SF1 and SF2, such that reactions with H$_2$S would generate highly fluorescent rhodamine dyes (Scheme 1). In their protected form, SF1 and SF2 adopt a closed lactone conformation and exhibit no absorption features in the visible region. Upon treatment of 10 μM SF1 or SF2 with 100 μM NaSH, a commonly employed H$_2$S donor, a robust increase in the fluorescence can be observed (Product from SF1: $\lambda_{em}$=525 nm, $\Phi$=0.51; Product from SF2: $\lambda_{em}$=525 nm, $\Phi$=0.60) accompanied by new absorbance bands in the visible region (Product from SF1: $\lambda_{max}$=490 nm, $\epsilon$=61,000 M$^{-1}$cm$^{-1}$; Product from SF2: $\lambda_{max}$=492 nm, $\epsilon$=75,000 M$^{-1}$cm$^{-1}$). After one hour of reaction under these conditions, SF1 and SF2 produced a 7-fold turn-on response (FIG. 1a) and 9-fold turn-on response (FIG. 1b), respectively. Although the reaction is only partially complete at this time point, a significant increase in fluorescence intensity is achieved due to the brightness of the product rhodamines. SF1 and SF2 display a selective turn-on response for H$_2$S relative to other biologically relevant reactive sulfur species (RSS), reactive oxygen species (ROS), and reactive nitrogen species (RNS) (FIG. 2). Both probes display high selectivity for H$_2$S over abundant biologically relevant thiols, including 5 mM glutathione and 5 mM cysteine (50× the amount of H₂S tested). Additionally, other relevant RSS including sulfite, thiosulfate, thiocyanate, S-nitroso glutathione, and lipoic acid, show negligible or small fluorescence responses. Lastly, SF1 and SF2 do not respond to most biologically relevant ROS or RNS, including hydrogen peroxide (H$_2$O$_2$), tert-butyl peroxide ($^t$BuOOH), hypochlorite (OCl$^-$), nitrite (NO$_2^-$), and nitric oxide (NO), and have good selectivity for H$_2$S versus superoxide (O$_2^-$). SF2 has more favorable fluorescence properties in vitro as compared to SF1, displaying a greater fluorescence response to H$_2$S, lower background reactivity to other analytes, and better selectivity versus glutathione, sulfite, and O$_2^-$. Taken together, these selectivity assays demonstrate that the chemoselective reduction of an azide to an amine can be used for the fluorescence detection of H$_2$S under aqueous conditions. The applicability of SF1 and SF2 for live-cell imaging of H$_2$S was demonstrated using confocal microscopy (FIG. 3). Living HEK293T cells were incubated with 5 μM SF1 or SF2 for 30 min, followed by treatment with 250 μM NaSH, a commonly employed H$_2$S donor, for 30 min. A patent increase in intracellular fluorescence intensity can be observed upon excitation at 488 nm (FIG. 3$b,e$). Comparison of the response of SF1 and SF2 in untreated cells demonstrates that there is little background response in the absence of exogenous H$_2$S, further confirming the selectivity of these probes against other biological species (FIG. 3$a,d$). Bright field images co-localized with Hoescht nuclear staining confirm the cell viability over the course of the experiments (FIG. 3$c,f$). Both probes demonstrate exceptional cellular permeability, with the urea derivative SF2 showing significant staining of the cellular nuclei (FIG. 3$e$). While the basal levels of H$_2$S are under debate, bolus additions of 30-400 μM NaSH are typically used to evoke a physiological response.$^{x,xi,xv}$ Our studies clearly demonstrate that SF1 and SF2 can effectively image H$_2$S concentrations within this range in living cells, and significant changes in fluorescence intensity can be seen at even lower concentrations (FIG. 4).

4-Azido-1,8-naphthalimide has also been synthesized as a fluorescent H$_2$S probe (Scheme 2) and exhibits a similar turn-on response as SF1 and SF2, but with a red-shifted emission (FIG. 5), demonstrating the tenability of azide probes to provide a palette of colors for H$_2$S detection. Several other azide-masked fluorophores have been synthesized (Scheme 3), including probes with varying emission wavelengths and probes that can be trapped intracellularly to provide signal enhancement. These and other probes could be useful both for the imaging of H$_2$S in live-cells using confocal microscopy as well as colorimetric and fluorescent assays for the precise detection of H$_2$S in a variety of samples.

Compositions

Also provided herein are compounds and compositions for detecting reactive sulfur species.

In one aspect, the invention provides a compound having the structure:

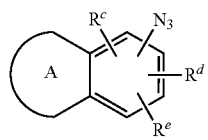

wherein A is a member selected from:

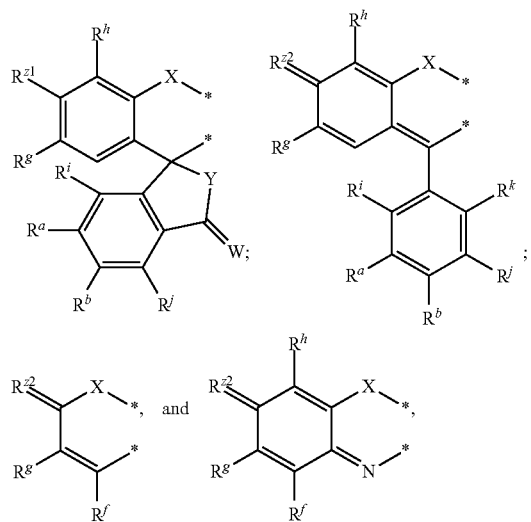

$R^a$ and $R^b$ are independently selected from H, —C(O)OR$^4$, —C(O)NR$^5$R$^6$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, halogen, —OR$^{11}$, —SR$^{11}$, —NR$^{12}$R$^{13}$, —C(O)OR$^{11}$, —CHO, —OSO$_3$R$^{11}$, and —C(O)NR$^{12}$R$^{13}$; wherein R$^4$, R$^5$, R$^6$, R$^{11}$, R$^{12}$ and R$^{13}$ are independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; wherein R$^5$ and R$^6$ are optionally joined to form, along with the atom to which they are attached, a substituted or unsubstituted heterocycloalkyl; and R$^{12}$ and R$^{13}$ are optionally joined to form, along with the atom to which they are attached, a substituted or unsubstituted heterocycloalkyl.

$R^c$, $R^d$, $R^e$, $R^f$, $R^g$, $R^h$, $R^i$, $R^j$, and $R^k$ are independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, halogen, —OR$^{11}$, —SR$^{11}$, —NR$^{12}$R$^{13}$, —C(O)OR$^{11}$, —CHO, —OSO$_3$R$^{11}$, and —C(O)NR$^{12}$R$^{13}$; wherein R$^{11}$, R$^{12}$ and R$^{13}$ are as defined herein.

$R^{z1}$ is a member selected from —OR$^3$, —SR$^3$, —NR$^1$R$^2$, -L$^1$R$^L$, —N$_3$—, —N(H)C(O)OR$^3$ and —N(H)C(O)NR$^1$R$^2$; wherein R$^1$, R$^2$ and R$^3$ are independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; wherein R$^1$ and R$^2$ are optionally joined to form, along with the atom to which they are attached, a substituted or unsubstituted heterocycloalkyl; L$^1$ is a linker which is a member selected from a bond, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; and $R^L$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

$R^{z2}$ is a member selected from O, S, $NR^1$, $N^+R^1R^2$, and $L^1R^L$; wherein $R^1$, $R^2$, $L^1$ and $R^L$ are as defined herein.

W is a member selected from O, $NR^7$, S, and Se; wherein $R^7$ is a member selected from H, substituted or unsubstituted alkyl, substituted or unsubstituted heteroalkyl.

X is a member selected from O, S, Se, $CR^8R^9$, and $SiR^8R^9$; wherein $R^8$ and $R^9$ are independently selected from H, substituted or unsubstituted alkyl, substituted or unsubstituted heteroalkyl.

Y is a member selected from O, $NR^{10}$, S, and Se; wherein $R^{10}$ is a member selected from H, substituted or unsubstituted alkyl, substituted or unsubstituted heteroalkyl.

In another aspect, the invention provides a compound having a structure selected from:

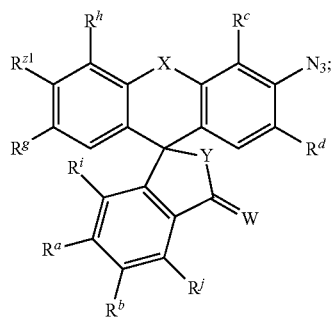

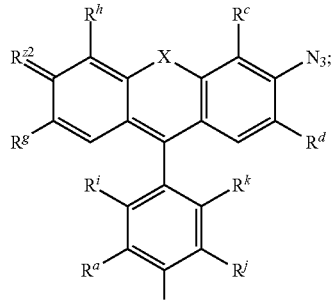

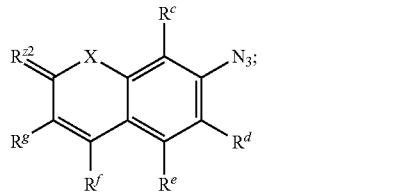

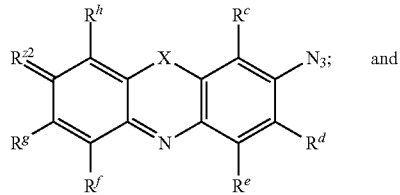

and

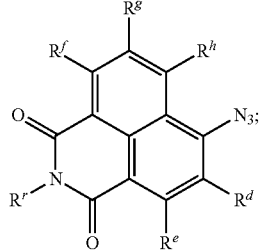

wherein $R^a$, $R^b$, $R^c$, $R^d$, $R^e$, $R^f$, $R^g$, $R^h$, $R^i$, $R^j$, $R^k$, $R^{z1}$, $R^{z2}$, W, X, and Y are as defined herein. $R^r$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

In some embodiments, invention provides a compound having a structure selected from:

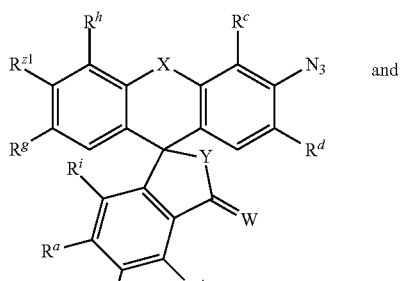

and

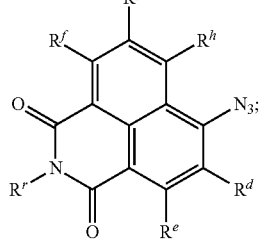

wherein $R^a$, $R^b$, $R^c$, $R^d$, $R^e$, $R^f$, $R^g$, $R^h$, $R^i$, $R^j$, $R^k$, $R^r$, $R^{z1}$, $R^{z2}$, W, X, and Y are as defined herein.

In some embodiments, invention provides a compound having a structure selected from:

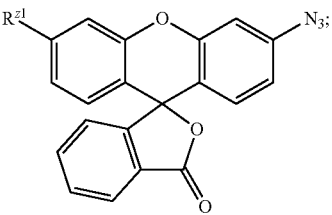

-continued
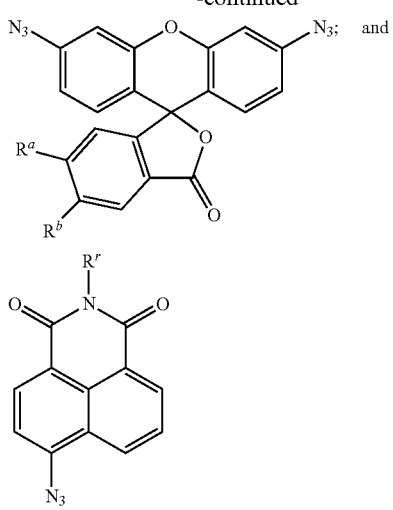
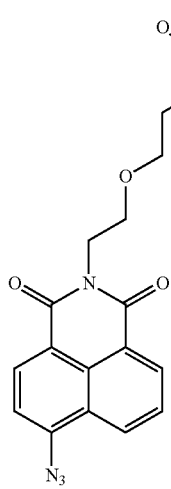
wherein $R^a$, $R^b$, $R^r$, and $R^{z1}$ are as defined herein.
In some embodiments, invention provides a compound having a structure selected from:
[SF1]
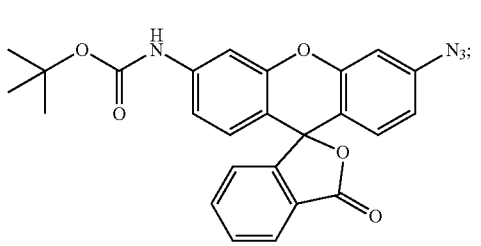
[SF2]
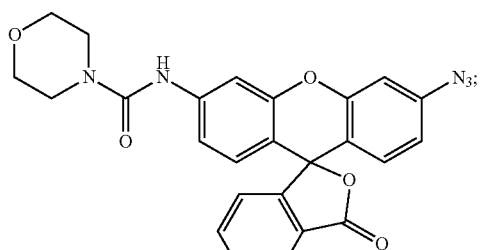
-continued
[SF4]
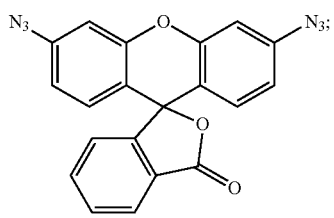
[SF5]
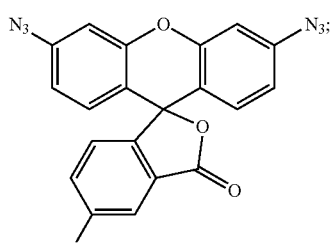
[SF5-AM]
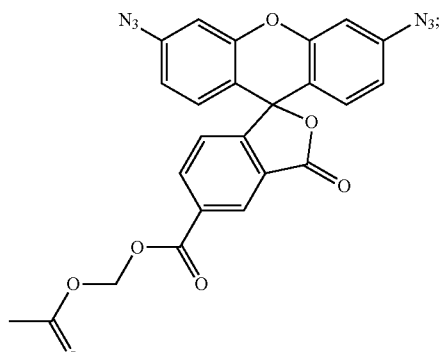
[SF6]
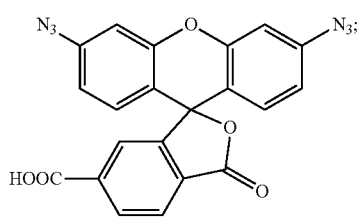
[SF6-AM]
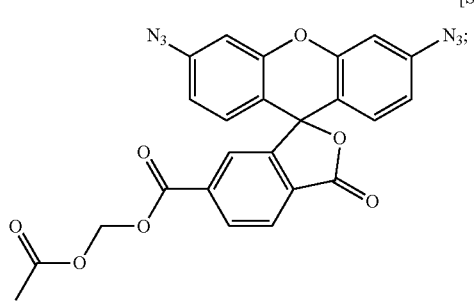

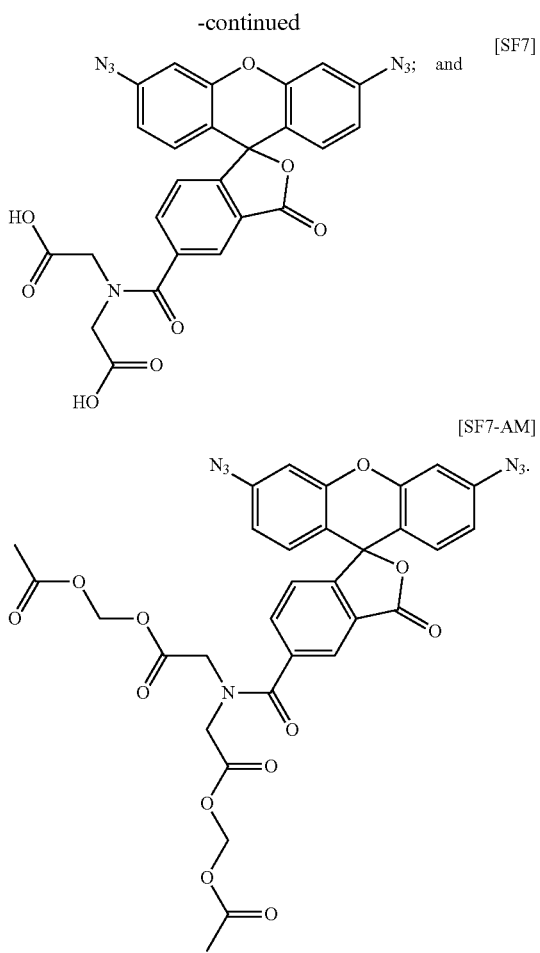

In some embodiments, $R^a$ and $R^b$ are independently selected from H, —C(O)OR$^4$, and —C(O)NR$^5$R$^6$; wherein R$^4$, R$^5$, and R$^6$ are as defined herein. In some embodiments, at least one of $R^a$ and $R^b$ is H. In some embodiments, $R^a$ is H. In some embodiments, $R^b$ is H.

In some embodiments, R$^4$ is a member selected from H, substituted or unsubstituted alkyl, and substituted or unsubstituted heteroalkyl. In some embodiments, R$^4$ is H. In some embodiments, R$^4$ is substituted C$_1$, C$_2$, C$_3$, C$_4$, C$_5$ or C$_6$ alkyl. In some embodiments, R$^4$ is C$_1$, C$_2$, C$_3$, C$_4$, C$_5$ or C$_6$ alkyl substituted with —OC(O)R$^{14}$, wherein R$^{14}$ is a member selected from unsubstituted C$_1$, C$_2$, C$_3$, C$_4$, C$_5$ or C$_6$ alkyl. In some embodiments, R$^4$ is acetoxymethyl.

In some embodiments, R$^5$ and R$^6$ are independently selected from H, substituted or unsubstituted alkyl, and substituted or unsubstituted heteroalkyl. In some embodiments, R$^5$, R$^6$ or both are alkyl substituted with —C(O)OR$^4$; wherein R$^4$ is as defined herein. In some embodiments, R$^5$, R$^6$ or both are C$_1$, C$_2$, C$_3$, C$_4$, C$_5$ or C$_6$ alkyl substituted with —C(O)OR$^4$.

In some embodiments, R$^c$, R$^d$, R$^e$, R$^f$, R$^g$, R$^h$, R$^i$, R$^j$, and R$^k$ are each H.

In some embodiments, R$^r$ is a member selected from substituted or unsubstituted alkyl and substituted or unsubstituted heteroalkyl. In some embodiments, R$^r$ is substituted heteroalkyl. In some embodiments, R$^r$ is heteroalkyl substituted with —OC(O)R$^{14}$, wherein R$^{14}$ is as defined herein. In some embodiments, R$^r$ is

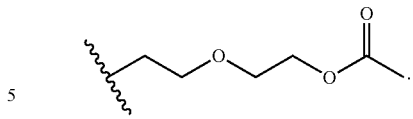

In some embodiments, R$^{z1}$ is a member selected from —NR$^1$R$^2$, —N$_3$, —N(H)C(O)OR$^3$ and —N(H)C(O)NR$^1$R$^2$; wherein R$^1$, R$^2$ and R$^3$ are as defined herein. In some embodiments, R$^{z1}$ is a member selected from —N(H)C(O)OR$^3$ and —N(H)C(O)NR$^1$R$^2$; wherein R$^1$, R$^2$ and R$^3$ are as defined herein. In some embodiments, R$^{z1}$ is —N(H)C(O)OR$^3$; wherein R$^3$ is as defined herein. In some embodiments, R$^{z1}$ is —N(H)C(O)NR$^1$R$^2$; wherein R$^1$ and R$^2$ are as defined herein.

In some embodiments, R$^3$ is substituted or unsubstituted alkyl. In some embodiments, R$^3$ is unsubstituted C$_1$, C$_2$, C$_3$, C$_4$, C$_5$, or C$_6$ alkyl. In some embodiments, R$^3$ is tert-butyl.

In some embodiments, R$^1$ and R$^2$ are independently selected from H, substituted or unsubstituted alkyl, and substituted or unsubstituted heteroalkyl. In some embodiments, R$^1$ and R$^2$ are joined to form, along with the atom to which they are attached, a substituted or unsubstituted heterocycloalkyl. In some embodiments, —R$^1$-R$^2$— is substituted or unsubstituted heteroalkanediyl. In some embodiments, —R$^1$-R$^2$— is —(CH$_2$)$_2$O(CH$_2$)$_2$—.

In some embodiments, W, X and Y are each O.

Enzymatically Cleavable Ester

In some embodiments, a compound of the invention comprises an ester moiety. In some embodiments, the ester moiety is an enzymatically cleavable ester. In some embodiments, R$^{z1}$ comprises an enzymatically cleavable ester. In some embodiments, one of R$^a$ and R$^b$ comprises an enzymatically cleavable ester. In some embodiments, R$^r$ comprises an enzymatically cleavable ester. In some embodiments, the enzymatically cleavable ester is an acetoxymethyl ester or an acetate ester. In some embodiments, the enzymatically cleavable ester is an acetoxymethyl ester.

Probes

In some embodiments, a compound disclosed herein is a probe for a reactive sulfur species. In some embodiments, the azide moiety of the compounds disclosed herein undergoes a reduction upon contact with the reactive sulfur species, generating a detectable signal. In some embodiments, the resulting reaction product is a flourophore. In some embodiments, the detectable signal is fluorescence.

In some embodiments, the reactive sulfur species is H$_2$S.

Reactions of various exemplary probes of the invention with H$_2$S are shown below.

Scheme. Sulfidefluor-1 (SF1) and
Sulfidefluor-2 (SF2) Fluorescent Probes for H$_2$S

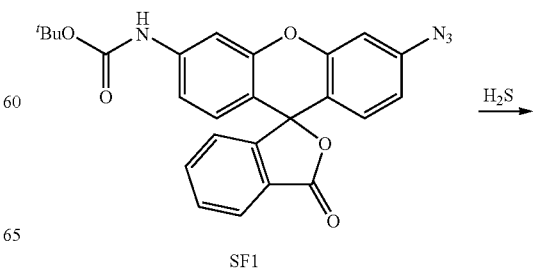

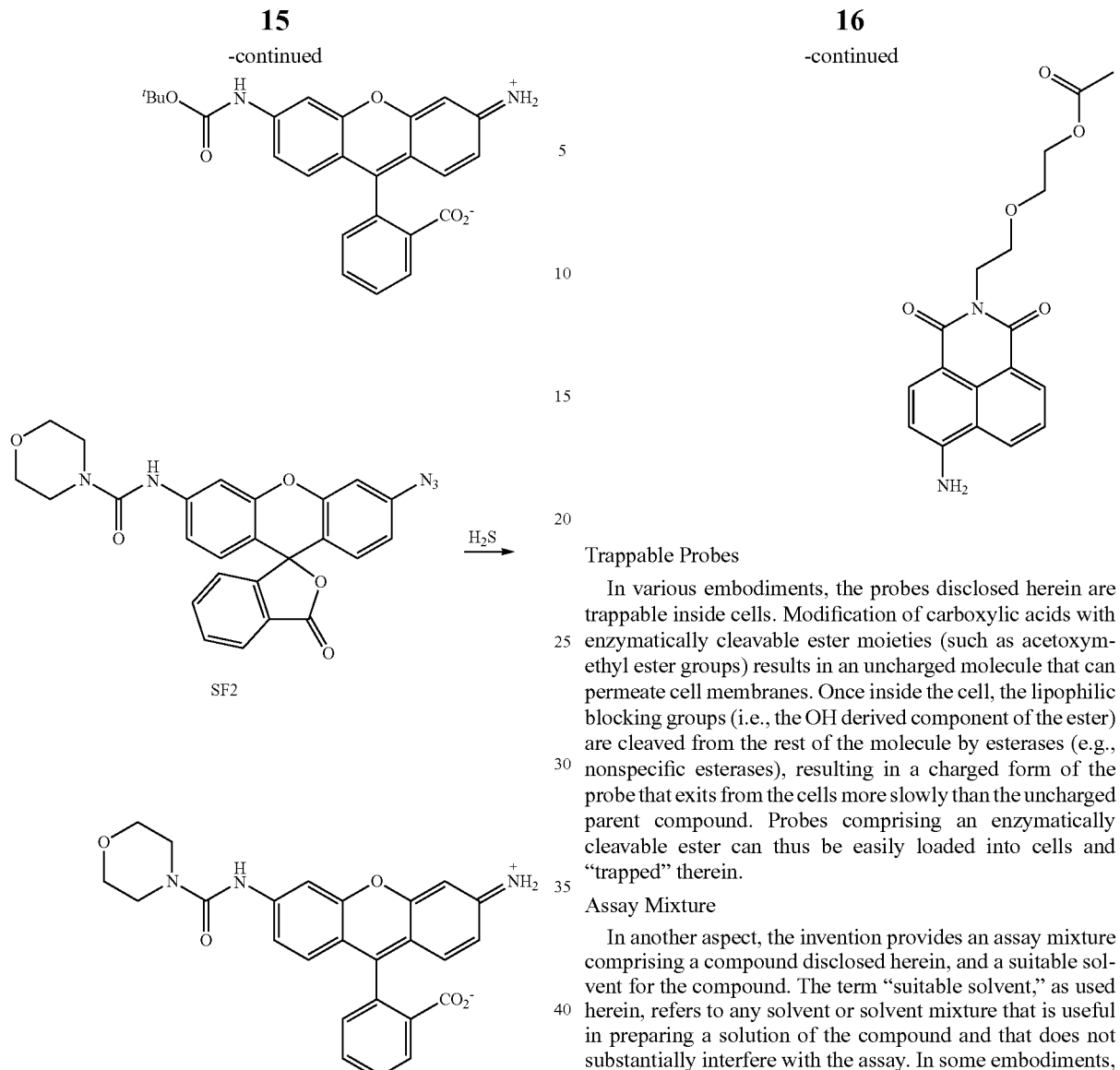

Scheme. 4-Azido-1,8-naphthalimide Probe for H₂S Detection.

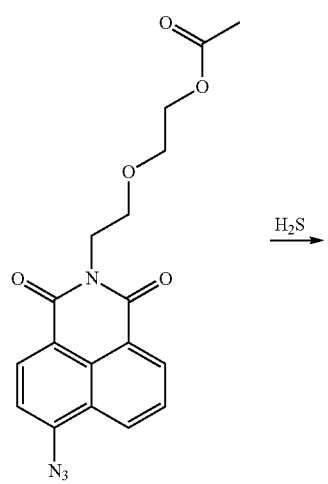

Trappable Probes

In various embodiments, the probes disclosed herein are trappable inside cells. Modification of carboxylic acids with enzymatically cleavable ester moieties (such as acetoxymethyl ester groups) results in an uncharged molecule that can permeate cell membranes. Once inside the cell, the lipophilic blocking groups (i.e., the OH derived component of the ester) are cleaved from the rest of the molecule by esterases (e.g., nonspecific esterases), resulting in a charged form of the probe that exits from the cells more slowly than the uncharged parent compound. Probes comprising an enzymatically cleavable ester can thus be easily loaded into cells and "trapped" therein.

Assay Mixture

In another aspect, the invention provides an assay mixture comprising a compound disclosed herein, and a suitable solvent for the compound. The term "suitable solvent," as used herein, refers to any solvent or solvent mixture that is useful in preparing a solution of the compound and that does not substantially interfere with the assay. In some embodiments, the suitable solvent is water-miscible. In some embodiments, the suitable solvent comprises a dispersing agent.

Methods

The compounds disclosed herein can be used in the real-time imaging of H₂S in living cells in various models of cardiovascular, neurodegenerative, and inflammatory diseases. These probes could be used for various applications in biochemical and biomedical research, enabling new methods to study the role of endogenously produced H₂S in living cellular models of health and disease. Additionally, these probes could be used in clinical and drug-development assays by providing a rapid method to assess the levels of H₂S in in vitro and in cellulo assays. The tunability of the color of the probes makes this technology amenable to the production of simple assays and test strips that could allow for rapid quantitative and semi-quantitative detection of H₂S in food samples, supplements, and clinical samples. Hence, there is great potential for commercialization in the food industry, the dietary supplement industry, and in the health and biomedical industry.

In another aspect, the invention provides a method of detecting a reactive sulfur species in a sample comprising: (a) contacting the sample with a probe disclosed herein; and (b) detecting the reaction product emitting a detectable signal.

In some embodiments, the reactive sulfur species is $H_2S$.

In some embodiments, the sample comprises a cell, and the reaction product is formed within the cell.

In some embodiments, the cell is a living cell.

In some embodiments, the reaction product is detected in real-time.

In another aspect, the invention provides a method of detecting a physiological process selected from vasodilation, angiogenesis, oxygen sensing, apoptosis, inflammation, and neuromodulation, the method comprising: (a) contacting the sample with a probe disclosed herein; and (b) detecting the reaction product emitting a detectable signal.

In another aspect, the invention provides a method of detecting a disease state in a patient, wherein the disease state is selected from Alzheimer's disease, Down's syndrome, diabetes, and cirrhosis of the liver, the method comprising: (a) contacting the sample with a probe disclosed herein; and (b) detecting the reaction product emitting a detectable signal.

([i]) Sies, H. *Free Radic. Biol. Med.* 1999, 27, 916-921.
([ii]) Estrela, J. M.; Ortega, A.; Obrador, E. *Crit. Rev. Clin. Lab. Sci.* 2006, 43, 143-181.
([iii]) Seth, D.; Stamler, J. S. *Curr. Opin. Chem. Biol.* 2007, 15, 1-8.
([iv]) Paulsen, C. E.; Caroll, K. S. *ACS Chem. Biol.* 2010, 5, 47-62.
([v]) Garrett, R. M.; Johnson, J. L.; Graf, T. N.; Feigenbaum, A.; Rajagopalan, K. V. *Proc. Natl. Acad. Sci. U.S.A.* 1998, 95, 6394-6398.
([vi]) Kabil, O.; Banerjee, R. *J. Biol. Chem.* 2010, 285, 21903-21907.
([vii]) Li, L.; Rose, P.; Moore, P. K. *Annu. Rev. Pharmacol. Toxicol.* 2011, 51, 169-187.
([viii]) Mustafa, A. K.; Gadalla, M. M.; Sen, N.; Kim, S.; Mu, W.; Gazi, S. K.; Barrow, R. K.; Yang, G.; Wang, R.; Snyder, S. H. *Sci. Signal.* 2009, 2, ra72.
([ix]) Blackstone, E.; Morrison, M.; Roth, M. B. *Science* 2005, 308, 518.
([x]) Yang, G.; Wu, L.; Jiang, B.; Yang, B.; Qi, J.; Cao, K.; Meng, Q.; Mustafa, A. K.; Mu, W.; Zhang, S.; Snyder, S. H.; Wang, R. *Science* 2008, 322, 587-590.
([xi]) Papapetropoulos, A.; Pyriochou, A.; Altaany, Z.; Yang, G.; Marazioti, A.; Zhou. Z.; Jeschke, M. G.; Branski, L. K.; Herndon, D. N.; Wang, R.; Szabo, C. *Proc. Natl. Acad. Sci. U.S.A.* 2009, 106, 21972-21977.
([xii]) Peng, Y.-J.; Nanduri, J.; Raghuraman, G.; Souvannakitti, D.; Gadalla, M. M.; Kumar, G. K. *Proc. Natl. Acad. Sci. U.S.A.* 2010, 107, 10719-10724.
([xiii]) Yang, G.; Wu, L.; Wang, R. *FASEB J.* 2006, 20, 553-555.
([xiv]) Li, L.; Bhatia, M.; Zhu, Y. Z.; Zhu, Y. C.; Ramnath, R. D.; Wang, Z. J.; Anuar, F. B.; Whiteman, M.; Salto-Tellez, M.; Moore, P. K. *FASEB J.* 2005, 19, 1196-1198.
([xv]) Abe, K.; Kimura, H. *J. Neurosci.* 1996, 16, 1066-1071.
([xvi]) Nicholson, C. K.; Calvert, J. W. *Pharmacol. Res.* 2010, 62, 289-297.
([xvii]) Eto, K.; Asada, T.; Arima, K.; Makifuchi, T.; Kimura, H. *Biochem. Biophys. Res. Commun.* 2002, 293, 1485-1488.
([xviii]) Kamoun, P.; Belardinelli, M.-C.; Chabli, A.; Lallouchi, K.; Chadefaux-Vekemans, B. *Am. J. Med. Genet.* 2003, 116A, 310-311.
([xix]) Yang, W.; Yang, G.; Jia, X.; Wu, L.; Wang, R. *J. Physiol.* 2005, 569, 519-531.
([xx]) Fiorucci, S.; Antonelli, E.; Mencarelli, A.; Orlandi, S.; Renga, B.; Rizzo, G.; Distrutti, E.; Shah, V.; Morelli, A. *Hepatology* 2005, 42, 539-548.
([xxi]) Fisher, E. *Chem. Ber.* 1883, 16, 2234-2236.
([xxii]) Choi, M. M. F. *Analyst* 1998, 123, 1631-1634.
([xxiii]) Choi, M. G.; Cha, S.; Lee, H.; Jeon, H. L.; Chang, S. K. *Chem. Commun.* 2009, 7390-7392.
([xxiv]) Lawrence, N. S.; Davis, J.; Jiang, L.; Jones, T. G. J.; Davies, S. N.; Compton, R. G. *Electroanlaysis* 2000, 18, 1453-1460.
([xxv]) Fume, J.; Saeed, A.; Levitt, M. D. *Am. J. Physiol. Regul. Integr. Comp. Physiol.* 2008, 295, R1479-1485.
([xxvi]) Ishigami, M.; Hiraki, K.; Umemura, K.; Ogasawara, Y.; Ishii, K.; Kimura, H. *Antioxid. Redox Signal.* 2009, 11, 205-214.
([xxvii]) Warenycia, M. W.; Goodwin, L. R.; Benishin, C. G.; Reiffenstein, R. J.; Francom, D. M.; Taylor, J. D.; Dieken, F. P. *Biochem. Pharmacol.* 1989, 38, 973-981.
([xxviii]) Han, Y.; Qin, J.; Chang, X.; Yang, Z.; Du, *J. Cell. Mol. Neurobiol.* 2006, 26, 101-107.

EXAMPLES

Example 1

SF1 and SF2

General Methods.

All reactions utilizing air- or moisture-sensitive reagents were performed in dried glassware under an atmosphere of dry $N_2$. Other reagents were used without further purification. Silica gel P60 (SiliCycle) was used for column chromatography and SiliCycle 60 F254 silica gel (precoated sheets, 0.25 mm thick) was used for analytical thin layer chromatography and visualized by fluorescence quenching under UV light or by staining with iodine. tert-Butoxycarbonyl-rhodamine 110 and morpholinourea-rhodamine 110 were synthesized according to literature procedures.[S1] All other reagents were purchased from Sigma-Aldrich (St. Louis, Mo.). $^1H$ NMR and $^{13}C$ NMR spectra for characterization of new compounds were collected in $CDCl_3$ (Cambridge Isotope Laboratories, Cambridge, Mass.) at 25° C. on a Bruker AVQ-400 spectrometer at the College of Chemistry NMR Facility at the University of California, Berkeley. All chemical shifts are reported in the standard δ notation of parts per million using the peak of residual proton signals of $CDCl_3$ or $d^6$-acetone as an internal reference. Splitting patterns are indicated as follows: br, broad; s, singlet; d, doublet; t, triplet; q, quartet; m, multiplet; dd, doublet of doublets; dt, doublet of triplets. Low-resolution mass spectral analyses were carried out using a LC-MS (Agilent Technology 6130, Quadrupole LC/MS). High-resolution mass spectral analyses (ESI-MS) were carried out at the College of Chemistry Mass Spectrometry Facility at the University of California, Berkeley.

Example 1.1

Synthesis

Scheme. Synthesis of Sulfidefluor-1 (SF1) and Sulfidefluor-2 (SF2).

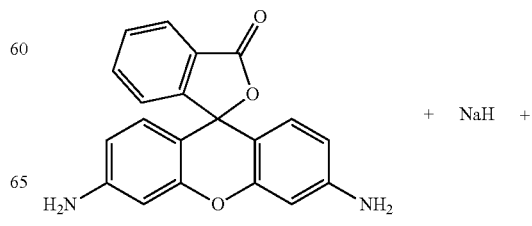

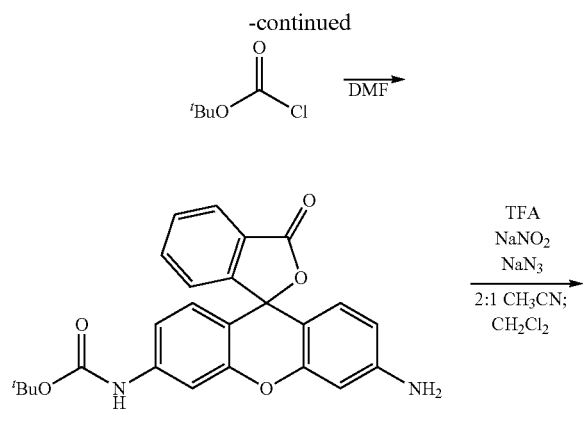

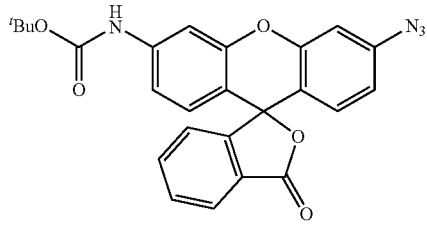

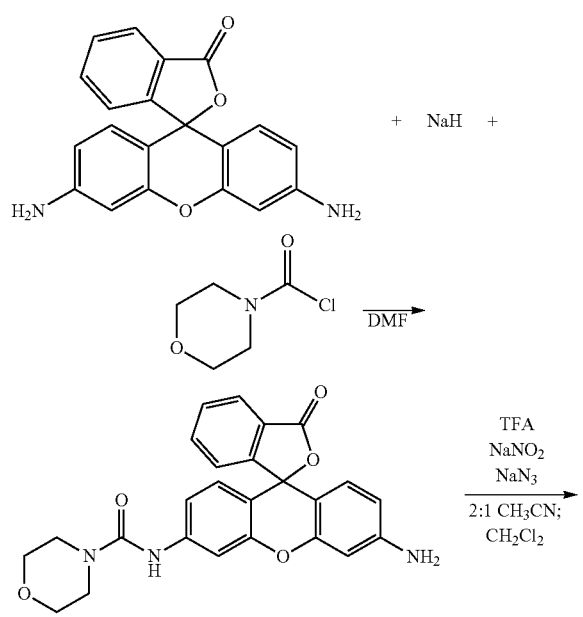

SF1

Sulfidefluor-1 (SF1).[S2]

tert-Butoxycarbonyl-rhodamine 110 (54.1 mg, 0.126 mmol, 1.0 equiv) was dissolved in 13.5 mL 2:1 CH3CN:CH2Cl2. Trifluoroacetic acid (13.5 µL, 0.182 mmol, 1.4 equiv) was added to give a red precipitate, followed directly by the addition of iso-amyl nitrite (20 µL, 0.15 mmol, 1.2 equiv) to give a yellow solution. After stirring for 2 h at ambient temperature, sodium azide (16.8 mg, 0.258 mmol, 2.1 equiv) was added and the solution was allowed to stir for an additional 1 h. The reaction mixture was then poured into 40 mL saturated aq NaHCO$_3$. The layers were separated and the aqueous layer was washed with an additional 2×40 mL EtOAc. The combined organic layers were dried over Na$_2$SO$_4$, filtered, and concentrated. The crude product was purified by silica column chromatography (4:1 Hex:EtOAc→1:1 Hex:EtOAc) to yield SF1 (40 mg, 70%). $^1$H NMR (400 MHz, CDCl$_3$) δ 8.02 (d, 1H, J=7.2 Hz), 7.67 (t, 1H, J=7.2 Hz), 7.62 (t, 1H, J=7.2 Hz), 7.55 (brs, 1H), 7.12 (d, 1H, J=7.2 Hz), 6.92 (d, 1H, J=1.9 Hz), 6.89 (dd, 1H, J=2.2, 8.8 Hz), 6.78 (s, 1H), 6.75 (s, 1H), 6.71 (d, 1H, J=3.2 Hz), 6.69 (brm, 1H), 6.67 (s, 1H), 1.52 (s, 9H); $^{13}$C NMR (100 MHz, CDCl$_3$) δ 169.44, 152.96, 152.31, 152.20, 151.57, 142.49, 140.74, 135.18, 129.88, 129.50, 128.48, 126.26, 125.13, 123.79, 115.55, 114.78, 114.29, 112.72, 107.22, 105.97, 82.70, 81.15, 28.20; LRMS calcd for C$_{25}$H$_{21}$N$_4$O$_5$ (M+H$^-$) 457.1512. found 457.2.

SF2

Sulfidefluor-2 (SF2).

Morpholinourea-rhodamine 110 (29.8 mg, 0.0672 mmol, 1.0 equiv) was dissolved in 7.2 mL 2:1 CH$_3$CN:CH$_2$Cl$_2$ and cooled to 0° C. Trifluoroacetic acid (7.5 µL, 0.098 mmol, 1.5 equiv) was added to give a red solution, followed directly by the addition of iso-amyl nitrite (10.7 µL, 0.0796 mmol, 1.2 equiv) to give an orange solution. After stirring for 2 h at ambient temperature, sodium azide (12.4 mg, 0.191 mmol, 2.8 equiv) was added and the solution was allowed to stir for an additional 1 h. The reaction mixture was then poured into 15 mL saturated aq NaHCO$_3$. The layers were separated and the aqueous layer was washed with an additional 2×10 mL EtOAc. The combined organic layers were dried over Na$_2$SO$_4$, filtered, and concentrated. The crude product was purified by silica column chromatography (4:1 Hex:

EtOAc→1:1 Hex:EtOAc) to yield SF2 (25.5 mg, 81%). $^1$H NMR (400 MHz, CDCl$_3$) δ 8.01 (d, 1H, J=7.2 Hz), 7.68 (t, 1H, J=7.0 Hz), 7.63 (t, 1H, J=7.4 Hz), 7.55 (d, 1H, J=2.1 Hz), 7.13 (d, 1H, J=7.4 Hz), 6.90 (m, 3H), 6.76 (d, 1H, 8.6 Hz), 6.70 (dd, 1H, J=8.5, 2.1 Hz), 6.62 (d, 1H, 8.6 Hz); $^{13}$C NMR (100 MHz, CDCl$_3$) δ 169.64, 154.53, 153.23, 152.26, 151.45, 142.64, 141.55, 135.31, 131.21, 129.94, 129.46, 128.21, 126.18, 125.13, 123.97, 115.71, 115.43, 114.83, 112.71, 107.39, 107.30, 66.46, 44.25, 29.67; HRMS calcd for C$_{25}$H$_{20}$N$_5$O$_5$ (M+H$^+$) 470.1459. found 470.1460.

Example 1.2

Spectroscopic Materials and Methods.

Millipore water was used to prepare all aqueous solutions. All spectroscopic measurements were performed in 20 mM HEPES buffer, pH 7.4. Fluorescence spectra were recorded on a Photon Technology International Quanta Master 4 L-format scanning spectrofluorometer (Lawrenceville, N.J.) equipped with an LPS-220B 75-W xenon lamp and power supply, A-1010B lamp housing with an integrated igniter, switchable 814 photon-counting/analog photomultiplier detection unit, and MD5020 motor driver. Samples for emission measurements were contained in 1-cm×0.1-cm quartz (1.5 mL volume, Starna, Atascadero, Calif.). Absorption spectra were recorded using a Varian Cary 50 spectrophotometer (Walnut Creek, Calif.).

FIG. 1. Absorbance spectra of (a) 10 μM SF1 (b) 10 μM SF2, and 10 μM of rhodamine products (c) tert-butoxycarbonyl-rhodamine 110 and (d) morpholinourea-rhodamine 110.

Example 1.3

Quantum Yields.

Quantum yields were determined using fluorescein as a standard according to a published method.[S3] For each compound and fluorescein, the absorbance spectra were measured within an absorbance range of 0.01 to 0.1. The quantum yield was calculated according to the equation: $\Phi_{sample}=\Phi_{standard}(Grad_{sample}/Grad_{standard})(\eta_{sample}/\eta_{standard})$, where $\Phi$ is the quantum yield, $\Phi_{standard}=0.95$ in 0.1 M NaOH, Grad is the slope of the plot of absorbance versus integrated emission intensity, and η is the refractive index of the solvent.

Example 1.4

SF1 and SF2 Fluorescence Responses to H$_2$S.

A 10 μM solution of SF1 or SF2 in 20 mM HEPES buffered to pH 7.4 was prepared from a 5 mM stock solution of SF1 or SF2 in DMF in a 1.5 mL eppendorf tube. 10 μL of 10 mM stock solution of NaSH in degassed (by bubbling N$_2$ for ~30 min) 20 mM HEPES buffered at pH 7.4 was added (for a final concentration of 100 μM) and the mixture was vortexed for 10 s and then transferred to a cuvette. Emission spectra ($\lambda_{ex}$=488 nm, $\lambda_{ex}$=498-700 nm) were collected at 10, 20, 30, 40, 50, and 60 min. The spectrum at t=0 was acquired from a 10 μM solution of SF1 or SF2 without the addition of NaSH.

FIG. 2. Fluorescence responses of (a) 10 μM SF1 and (b) 10 μM SF2 to 100 μM H$_2$S. Data were acquired at 25° C. in 20 mM HEPES buffered to pH 7.4 with excitation at $\lambda_{ex}$=488 nm. Emission was collected between 498 and 700 nm. Time points represent 0, 10, 20, 30, 40, 50, and 60 min (red trace) after addition of 100 μM H$_2$S. Reactions are not complete at these time points.

Example 1.5

Detection Limit.

The detection limit of SF1 and SF2 was determined as the concentration of H$_2$S that resulted in a statistically significant increase in fluorescence intensity after 60 min with a p-value<0.01 when compared with a blank control.

FIG. 3. Fluorescence responses of (a) 10 μM SF1 and (b) 10 μM SF2 to 0, 5, and 10 μM H2S after 60 min. Data were acquired at 25° C. in 20 mM HEPES buffered to pH 7.4 with excitation at $\lambda_{ex}$=488 nm. Statistical analyses were performed with a two-tailed Student's t-test (n=3). Error bars are ±standard deviation.

Example 1.6

$^1$H NMR Analyses of the Reaction of SF1 and SF2 with H$_2$S.

A 5 mL reaction mixture of 500 μM SF1 or SF2 and 10 mM NaSH in 20 mM HEPES buffered to pH 7.4 with 1% DMF was stirred for 1 h. The fluorescent reaction mixtures were concentrated and $^1$H NMR spectra were acquired in CD$_3$OD.

FIG. 4. 1H NMR (400 MHz, CD$_3$OD) spectra of (a) SF1, (b) the reaction of 500 μM SF1 with 10 mM NaSH, (c) tert-Butoxycarbonyl-rhodamine 110, (d) SF2, (e) the reaction of 500 μM SF2 with 10 mM NaSH, and (f) morpholinourea-rhodamine 110. Reactions are not complete at these early time points.

Example 1.7

Selectivity Tests.

Selectivities for the SF1 and SF2 probes were measured by fluorescence responses ($\lambda_{ex}$=488 nm, $\lambda_{em}$=525 nm) at 0, 15, 30, 45, and 60 min. All assays were performed in 20 mM HEPES buffered to pH 7.4.

H$_2$S: 10 μL of a 10 mM stock solution of NaSH in degassed HEPES was added to 10 μM SF1 or SF2 in HEPES with 0.2% DMF.

Glutathione and cysteine: 2 μL of 5 mM SF1 or SF2 in DMF was added to 998 μL 5 mM glutathione or cysteine HEPES.

Lipoic acid: 10 μL of a 10 mM stock solution of lipoic acid in HEPES was added to 990 μL of 10 μM SF1 or SF2 in HEPES with 0.2% DMF.

Na$_2$SO$_3$: 10 μL of a 10 mM stock solution of Na$_2$SO$_3$ in HEPES was added to 990 μL of 10 μM SF1 or SF2 in HEPES with 0.2% DMF.

NaS$_2$O$_3$: 10 μL of a 10 mM stock solution of NaS$_2$O$_3$ in HEPES was added to 990 μL of 10 μM SF1 or SF2 in HEPES with 0.2% DMF.

KSCN: 10 μL of a 10 mM stock solution of KSCN in HEPES was added to 990 μL of 10 μM SF1 or SF2 in HEPES with 0.2% DMF.

S-nitrosoglutathione:[S4] 10 μL of a 10 mM stock solution of S-nitroso glutathione in HEPES was added to 990 μL of 10 μM SF1 or SF2 in HEPES with 0.2% DMF.

NaNO$_2$: 10 μL of a 10 mM stock solution of NaNO$_2$ in HEPES was added to 990 μL of 10 μM SF1 or SF2 in HEPES with 0.2% DMF.

NO: 5 μL of a 10 mM stock solution of Proli-NONOATE in degassed (by bubbling N$_2$ for ~30 min) 10 mM NaOH in HEPES was added to 995 μL of a degassed (by bubbling N$_2$ for ~30 min) solution of 10 μM SF1 or SF2 in HEPES with 0.2% DMF.

H$_2$O$_2$: 10 μL of a 10 mM stock solution of H2O2 in HEPES was added to 990 μL of 10 μM SF1 or SF2 in HEPES with 0.2% DMF.

O₂⁻: 100 μL of a saturated solution of KO2 in DMSO (~1 mM) was added to 900 μL of 10 μM SF1 or SF2 in HEPES with 0.2% DMF.

ᵗBuOOH: 10 μL of a 10 mM stock solution of tBuOOH in HEPES buffered to was added to 990 μL of 10 μM SF1 or SF2 in HEPES with 0.2% DMF.

HOCl: 10 μL of a 10 mM stock solution of HOCl in HEPES was added to 990 μL of 10 μM SF1 or SF2 in HEPES with 0.2% DMF.

FIG. 5. Fluorescence responses of (a) 10 μM SF1 and (b) 10 μM SF2 to biologically relevant RSS, RNS, and ROS. Bars represent relative responses at 525 nm at 0, 15, 30, 45, and 60 min after addition of RSS, RNS, or ROS. Data shown are for 5 mM glutathione, 5 mM cysteine, and 100 μM for other RSS, RNS, and ROS. Data were acquired in 20 mM HEPES buffered at pH 7.4 with excitation at $\lambda_{ex}$=488 nm. 1. $H_2S$; 2. glutathione; 3. cysteine; 4. lipoic acid; 5. $Na_2SO_3$; 6. $NaS_2O_3$; 7. KSCN; 8. S-nitroso glutathione; 9. $NaNO_2$; 10. NO; 11. $H_2O_2$; 12. $O_2^-$; 13. ᵗBuOOH; 14. HOCl.

Example 1.8

Cell Culture and Labeling Procedures.

HEK 293T cells were maintained in exponential growth as a monolayer in Dulbecco's Modified Eagle Medium (DMEM, Invitrogen) supplemented with 10% fetal bovine serum (FBS, Hyclone), and incubated at 37° C. in 5% $CO_2$. One or two days before imaging, the cells were passaged and plated in phenol red-free medium on 4-well Lab-Tek borosilicate chambered coverglass slides (Nunc) and allowed to grow to 50-70% confluence. For all experiments, solutions of SF1 and SF2 were prepared in DMF (5 mM) and diluted into DMEM at the desired working concentrations (5 μM). NaSH was delivered from a stock solution of 25 mM in degassed (by bubbling $N_2$ for ~30 min) Dulbecco's Phosphate Buffered Saline (DPBS). Cells were treated with SF1 or SF2 for one hour, with NaSH (50-250 μM) or blank control added for the final 30 minutes. Images were collected at 30 min after NaSH addition. For nuclear imaging studies, cells were incubated with 1 μM Hoechst 33342 at 37° C. for 30 min prior to imaging.

Example 1.9

Confocal Imaging Experiments. Confocal fluorescence imaging studies were performed with a Zeiss laser scanning microscope 710 with a 40× water objective lens, with Zen 2009 software (Carl Zeiss). SF1 and SF2 were excited using a 488 nm Ar laser, and emission collected using a META detector between 500 and 650 nm. Hoechst 33342 was excited with a 405 nm diode laser, and emission collected using a META detector between 450 and 500 nm. The cells were imaged at 37° C. and 5% CO2 throughout the course of the experiment. Image analysis was performed using ImageJ (National Institute of Health).

Figure 6:
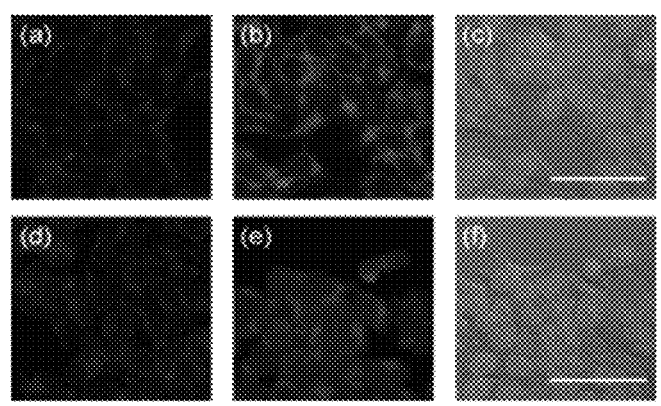
FIG. 6. Confocal images of $H_2S$ detection in live HEK293T cells using SF1 and SF2. (a) HEK293T cells incubated with SF1 for 60 min at 37° C. (b) HEK293T cells incubated with SF1 for 60 min at 37° C. with 250 μM NaSH added for the final 30 min. (c) Brightfield images of the same field of cells in (b) overlaid with images of 1 μM Hoescht stain at 37° C. (d) HEK293T cells incubated with SF2 for 60 min at 37° C. (e) HEK293T cells incubated with SF2 for 60 min at 37° C. with 250 μM NaSH added for the final 30 min. (f) Brightfield images of the same field of cells in (e) overlaid with images of 1 μM Hoescht stain at 37° C. Scale bars represent 50 μM.
Figure 8:
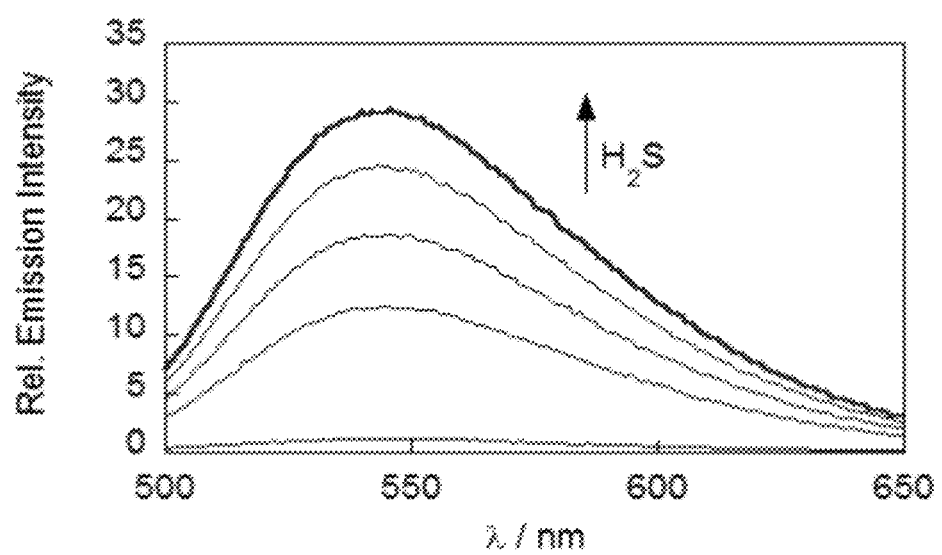
FIG. 8. Fluorescence response of 10 μM 4-azido-1,8-naphthalimide to 100 μM H$_2$S. Data were acquired at 25° C. in 20 mM HEPES buffered to pH 7.4 with excitation at $\lambda_{ex}$=470 nm. Emission was collected between 495 and 650 nm. Time points represent 0, 15, 30, 45, and 60 min (red trace) after addition of 100 μM H$_2$S. Reactions are not complete at these time points.

FIG. 6. Confocal images of $H_2S$ detection in live HEK293T cells using SF1 and SF2. (a) HEK293T cells incubated with SF1 for 60 min at 37° C. (b) HEK293T cells incubated with SF1 for 60 min at 37° C. with 250 μM NaSH added for the final 30 min. (c) Brightfield images of the same field of cells in (b) overlaid with images of 1 μM Hoescht stain at 37° C. (d) HEK293T cells incubated with SF2 for 60 min at 37° C. (e) HEK293T cells incubated with SF2 for 60 min at 37° C. with 250 μM NaSH added for the final 30 min. (f) Brightfield images of the same field of cells in (e) overlaid with images of 1 μM Hoescht stain at 37° C. Scale bars represent 50 μM.

FIG. 7. Mean fluorescence intensity of confocal images of $H_2S$ detected in live HEK293T cells treated with 0, 50, 100, and 250 μM $H_2S$. (a) HEK293T cells were incubated with SF1 for 60 min at 37° C. with the indicated amount of $H_2S$ added for the final 30 min. (b) HEK293T cells were incubated with SF2 for 60 min at 37° C. with the indicated amount of $H_2S$ added for the final 30 min. Data represent the mean fluorescence intensity of distinct fields (n=4). Error bars are ±s.e.m.

Example 1.10

Determination of Log P.

Lipophilicity was measured as the relative partitioning of the complex between HEPES (20 mM, pH 7.4) and 1-octanol. HEPES was pre-saturated with 1-octanol, and vice versa. SF1 and SF2 were prepared as 30 μM solutions in 1-octanol and mixed with water to give 1:2, 1:1, and 2:1 water:octanol ratios with final probe concentrations of 5 μM. Mixtures were agitated for fifteen hours, after which time emission spectra of the water and 1-octanol layers were collected ($\lambda_{ex}$=488 nm). The probe concentration in each solvent was calculated based on the integrated emission intensity with reference to calibration curves constructed for at least five concentrations between 0 and 0.5 μM for HEPES and 0 and 5 μM for 1-octanol. For each mixture, the log P value was calculated according to the equation:

$$\log P = \log_{10}(([X]_{1\text{-}octanol})/([X]_{HEPES}))$$

Final log P values were calculated as the average of at least two replicates of the three solvent mixtures.

Example 2

SF4, SF5, SF5-AM, SF6, SF6-AM, SF7 and SF7-AM

General Methods.

All reactions utilizing air- or moisture-sensitive reagents were performed in dried glassware under an atmosphere of dry $N_2$. Other reagents were used without further purification. Silica gel P60 (SiliCycle) was used for column chromatography and SiliCycle 60 F254 silica gel (precoated sheets, 0.25 mm thick) was used for analytical thin layer chromatography and visualized by fluorescence quenching under UV light or by staining with iodine. All other reagents were purchased from Sigma-Aldrich (St. Louis, Mo.). ¹H NMR and ¹³C NMR spectra for characterization of new compounds were collected in $CDCl_3$ (Cambridge Isotope Laboratories, Cambridge, Mass.) at 25° C. on a Bruker AVQ-400 spectrometer at the College of Chemistry NMR Facility at the University of California, Berkeley. All chemical shifts are reported in the standard δ notation of parts per million using the peak of residual proton signals of $CDCl_3$ or $CD_3OD$ as an internal reference. Splitting patterns are indicated as follows: br, broad; s, singlet; d, doublet; t, triplet; q, quartet; m, multiplet; dd, doublet of doublets; dt, doublet of triplets. Low-resolution mass spectral analyses were carried out using a LC-MS (Agilent Technology 6130, Quadrupole LC/MS). High-resolution mass spectral analyses (ESI-MS) were carried out at the College of Chemistry Mass Spectrometry Facility at the University of California, Berkeley.
Example 2.1
Synthesis
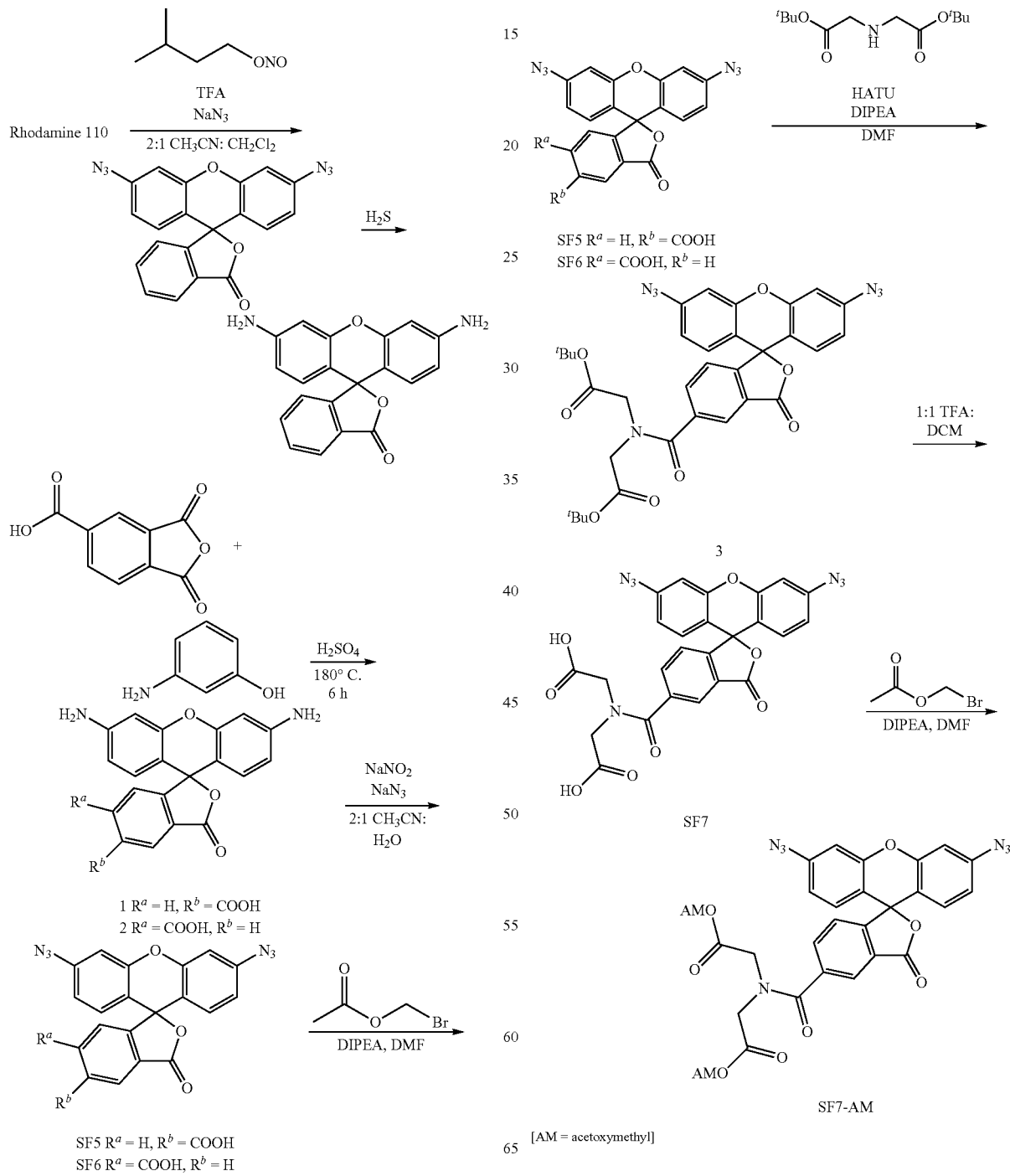
Scheme. Synthesis of trappable probes for H₂S imaging.
[AM = acetoxymethyl]

Carboxy rhodamines 1,2 (3',6'-diamino-3-oxo-3H-spiro[isobenzofuran-1,9'-xanthene]-5-carboxylic acid; 3',6'-diamino-3-oxo-3H-spiro[isobenzofuran-1,9'-xanthene]-6-carboxylic acid)

Aminophenol (3.60 g, 33.0 mmol, 2.96 equiv) was dissolved in 20 mL $H_2SO_4$ in a sealable pressure flask. Trimellitic anhydride (2.14 g, 11.1 mmol, 1 equiv) was added and the flask was closed and heated at 180° C. for 6 h. After cooling to rt, the reaction mixture was poured into 400 mL $CH_3CN$ while stirring at 0° C. A red ppt formed, which was filtered using a buchner funnel. The red-orange solids were washed with 6×50 mL $CH_3CN$ and then dried to yield 6.28 g (150%) of carboxy rhodamine 1 as red-orange solids and was used in the next step without further purification. 5'-carboxy rhodamine: $^1$H NMR (400 MHz, $CD_3OD$) δ 8.70 (s, 1H), 8.15 (d, 2H, J=8.0 Hz), 7.21 (d, 1H, J=8.0 Hz), 7.19 (s, 1H), 7.18 (s, 1H), 6.77 (m, 4H).

SF5, SF6 (3',6'-diazido-3-oxo-3H-spiro[isobenzofuran-1,9'-xanthene]-5-carboxylic acid, 3',6'-diazido-3-oxo-3H-spiro[isobenzofuran-1,9'-xanthene]-6-carboxylic acid)

Carboyxy rhodamine 1 (443.6 mg, 1.18 mmol, 1 equiv) was dissolved in 24 mL 2:1 $CH_3CN:H_2O$ and cooled to 0° C. Trifluoroacetic acid (0.2 mL, 2.6 mmol, 2.2 equiv) and sodium nitrite (184 mg, 2.67 mmol, 2.26 equiv) were added and the reaction was stirred at 0° C. for 24 min. Sodium azide (183.6 mg, 2.82 mmol, 2.39 equiv), the reaction was warmed to rt and allowed to stir for 30 min. The reaction was poured into 40 mL $H_2O$ and extracted with 3×40 mL EtOAC. The combined organic extracts were washed with 40 mL brine, dried over $Na_2SO_4$, filtered and concentrated. Purification by silica column chromatography (5% MeOH in $CH_2Cl_2$) provided an isomeric mixture of SF5 and SF6 (33.2 mg, 6.7%, 10% over 2 steps). Analytically pure samples and separation of isomers for spectroscopic characterization were obtained by preparative HPLC chromatography. SF5: $^1$H NMR (400 MHz, 1:1 $CDCl_3:CD_3OD$) δ 8.66 (s, 1H), 8.36 (d, 1H, J=8.0 Hz), 7.23 (d, 1H, J=8.0 Hz), 6.96 (brs, 2H), 6.76 (m, 4H); $^{13}$C NMR (100 MHz, 1:1 $CDCl_3:CD_3OD$) δ 168.73, 166.71, 156.13, 151.78, 143.11, 136.69, 133.59, 129.35, 126.89, 126.39, 123.94, 115.27, 114.51, 107.23, 82.29; HRMS-ESI calcd for $C_{21}H_9N_6O_5$ (M–H$^+$) 425.0640. found 425.0627.

SF5-AM (acetoxymethyl 3',6'-diazido-3-oxo-3H-spiro[isobenzofuran-1,9'-xanthene]-5-carboxylate)

$^1$H NMR (400 MHz, $CDCl_3$) δ 8.74 (s, 1H), 8.38 (d, 2H, J=8 Hz), 7.24 (d, 2H, J=8 Hz), 6.98 (s, 2H), 6.76 (dd, 4H, J=8 Hz, J=12 Hz), 6.05 (s, 2H), 2.18 (s, 3H); $^{13}$C NMR (100 MHz, $CDCl_3$) δ 169.6, 167.9, 163.7, 157.1, 151.8, 143.2, 136.6, 131.6, 129.4, 127.6, 126.7, 124.3, 115.4, 114.6, 107.4, 81.8, 80.1, 20.6; HRMS-ESI calcd for $C_{24}H_{15}N_6O_7$ (M+H$^+$) 499.0997. found 499.1010.

Carboxamide 3 (3',6'-diamino-3-oxo-3H-spiro[isobenzofuran-1,9'-xanthene]-6-carboxylic acid)

$^1$H NMR (400 MHz, $CDCl_3$) δ 8.12 (s, 1H), 7.81 (d, 1H, J=7.7 Hz), 7.19 (d, 1H, J=7.7 Hz), 6.97 (s, 2H), 6.77 (m, 4H), 4.25 (s, 2H), 4.02 (s, 2H), 1.52 (s, 9H), 1.49 (s, 9H); $^{13}$C NMR (100 MHz, $CDCl_3$) δ 70.1, 167.8, 167.7, 154.3, 151.8, 143.1, 137.4, 134.4, 129.4, 126.3, 124.3, 123.7, 115.3, 114.9, 107.3, 83.3, 82.4, 81.7, 52.7, 49.3, 28.1, 28.0; LRMS-ESI calcd for $C_{33}H_{32}N_7O_8$ (M+H$^+$) 654.2312. found 654.3.

SF7 (2,2'-((3',6'-diazido-3-oxo-3H-spiro[isobenzofuran-1,9'-xanthene]-5-ylcarbonyl)azanediyl)diacetic acid)

HRMS-ESI calcd for $C_{25}H_{16}N_7O_8$ (M+H$^+$) 542.1055. found 542.1068.

SF7-AM (bis(acetoxymethyl) 2,2'-((3',6'-diazido-3-oxo-3H-spiro[isobenzofuran-1,9'-xanthen]-5-ylcarbonyl)azanediyl)diacetate)

$^1$H NMR (400 MHz, $CDCl_3$) δ 8.08 (s, 1H), 7.79 (d, 1H, J=8.0 Hz), 7.22 (d, 1H, J=8.0 Hz), 6.98 (d, 2H, J=2.0 Hz), 6.82 (d, 2H, J=8.5 Hz), 6.78 (dd, 2H, J=8.5 Hz, J=2.0 Hz), 5.84 (s, 2H), 5.80 (s, 2H), 4.41 (s, 2H), 4.23 (s, 2H), 2.17 (s, 3H), 2.13 (s, 3H)

Example 2.2

Spectroscopic Materials and Methods.

Millipore water was used to prepare all aqueous solutions. All spectroscopic measurements were performed in 20 mM HEPES buffer, pH 7.4. Fluorescence spectra were recorded on a Photon Technology International Quanta Master 4 L-format scanning spectrofluorometer (Lawrenceville, N.J.) equipped with an LPS-220B 75-W xenon lamp and power supply, A-1010B lamp housing with an integrated igniter, switchable 814 photon-counting/analog photomultiplier detection unit, and MD5020 motor driver. Samples for emission measurements were contained in 1-cm×0.1-cm quartz (1.5 mL volume, Starna, Atascadero, Calif.). Absorption spectra were recorded using a Varian Cary 50 spectrophotometer (Walnut Creek, Calif.).

Example 2.3

Quantum Yields and Extinction Coefficients.

Quantum yields were determined using fluorescein as a standard according to a published method.[53] For each compound and fluorescein, the absorbance spectra were measured within an absorbance range of 0.01 to 0.1. The quantum yield was calculated according to the equation: $\Phi_{sample} = \Phi_{standard} (Grad_{sample}/Grad_{standard})(\eta_{sample}/\eta_{standard})$; where $\Phi$ is the quantum yield, $\Phi_{standard}$=0.95 in 0.1 M NaOH, Grad is the slope of the plot of absorbance versus integrated emission intensity, and η is the refractive index of the solvent.

Example 2.4

SF4, SF5, and SF7 Fluorescence Responses to $H_2S$.

A 10 μM solution of SF4, SF5, and SF7 in 20 mM HEPES buffered to pH 7.4 was prepared from a 5 mM stock solution of SF4, SF5, and SF7 in DMF in a 1.5 mL eppendorf tube. 10 μL of 10 mM stock solution of NaSH in degassed (by bubbling $N_2$ for ~30 min) 20 mM HEPES buffered at pH 7.4 was added (for a final concentration of 100 μM) and the mixture was vortexed for 10 s and then transferred to a cuvette. Emission spectra ($\lambda_{ex}$=488 nm, $\lambda_{ex}$=498-700 nm) were collected at 10, 20, 30, 40, 50, and 60 min. The spectrum at t=0 was acquired from a 10 μM solution of SF4, SF5, and SF7 without the addition of NaSH.

FIG. 9(a-c).

Fluorescence responses of (a) 10 μM SF4 (b) 10 μM SF5 and (c) 10 μM SF7 to 100 μM $H_2S$. Data were acquired at 25°

C. in 20 mM HEPES buffered to pH 7.4 with excitation at $\lambda_{ex}$=488 nm. Emission was collected between 498 and 700 nm. Time points represent 0, 10, 20, 30, 40, 50, and 60 min (red trace) after addition of 100 μM $H_2S$.

Example 2.5

Selectivity Tests.

Selectivities for the SF4, SF5, and SF7 probes were measured by fluorescence responses ($\lambda_{ex}$=488 nm, $\lambda_{em}$=525 nm) at 0, 15, 30, 45, and 60 min. All assays were performed in 20 mM HEPES buffered to pH 7.4.

$H_2S$: 10 μL of a 10 mM stock solution of NaSH in degassed HEPES was added to 10 μM SF4, SF5, and SF7 in HEPES with 0.2% DMF.

Glutathione and cysteine: 2 μL of 5 mM SF4, SF5, and SF7 in DMF was added to 998 μL 5 mM glutathione or cysteine HEPES.

Lipoic acid: 10 μL of a 10 mM stock solution of lipoic acid in HEPES was added to 990 μL of 10 μM SF4, SF5, and SF7 in HEPES with 0.2% DMF.

$Na_2SO_3$: 10 μL of a 10 mM stock solution of $Na_2SO_3$ in HEPES was added to 990 μL of 10 μM SF4, SF5, and SF7 in HEPES with 0.2% DMF.

$NaS_2O_3$: 10 μL of a 10 mM stock solution of $NaS_2O_3$ in HEPES was added to 990 μL of 10 μM SF4, SF5, and SF7 in HEPES with 0.2% DMF.

KSCN: 10 μL of a 10 mM stock solution of KSCN in HEPES was added to 990 μL of 10 μM SF4, SF5, and SF7 in HEPES with 0.2% DMF.

S-nitrosoglutathione:[S4] 10 μL of a 10 mM stock solution of S-nitroso glutathione in HEPES was added to 990 μL of 10 μM SF4, SF5, and SF7 in HEPES with 0.2% DMF.

$NaNO_2$: 10 μL of a 10 mM stock solution of $NaNO_2$ in HEPES was added to 990 μL of 10 μM SF4, SF5, and SF7 in HEPES with 0.2% DMF.

NO: 5 μL of a 10 mM stock solution of Proli-NONOATE in degassed (by bubbling $N_2$ for ~30 min) 10 mM NaOH in HEPES was added to 995 μL of a degassed (by bubbling $N_2$ for ~30 min) solution of 10 μM SF4, SF5, and SF7 in HEPES with 0.2% DMF.

$H_2O_2$: 10 μL of a 10 mM stock solution of $H_2O_2$ in HEPES was added to 990 μL of 10 μM SF4, SF5, and SF7 in HEPES with 0.2% DMF.

$O_2^-$: 100 μL of a saturated solution of $KO_2$ in DMSO (~1 mM) was added to 900 μL of 10 μM SF4, SF5, and SF7 in HEPES with 0.2% DMF.

$^tBuOOH$: 10 μL of a 10 mM stock solution of $^tBuOOH$ in HEPES buffered to was added to 990 μL of 10 μM SF4, SF5, and SF7 in HEPES with 0.2% DMF.

HOCl: 10 μL of a 10 mM stock solution of HOCl in HEPES was added to 990 μL of 10 μM SF4, SF5, and SF7 in HEPES with 0.2% DMF.

Figure 9:
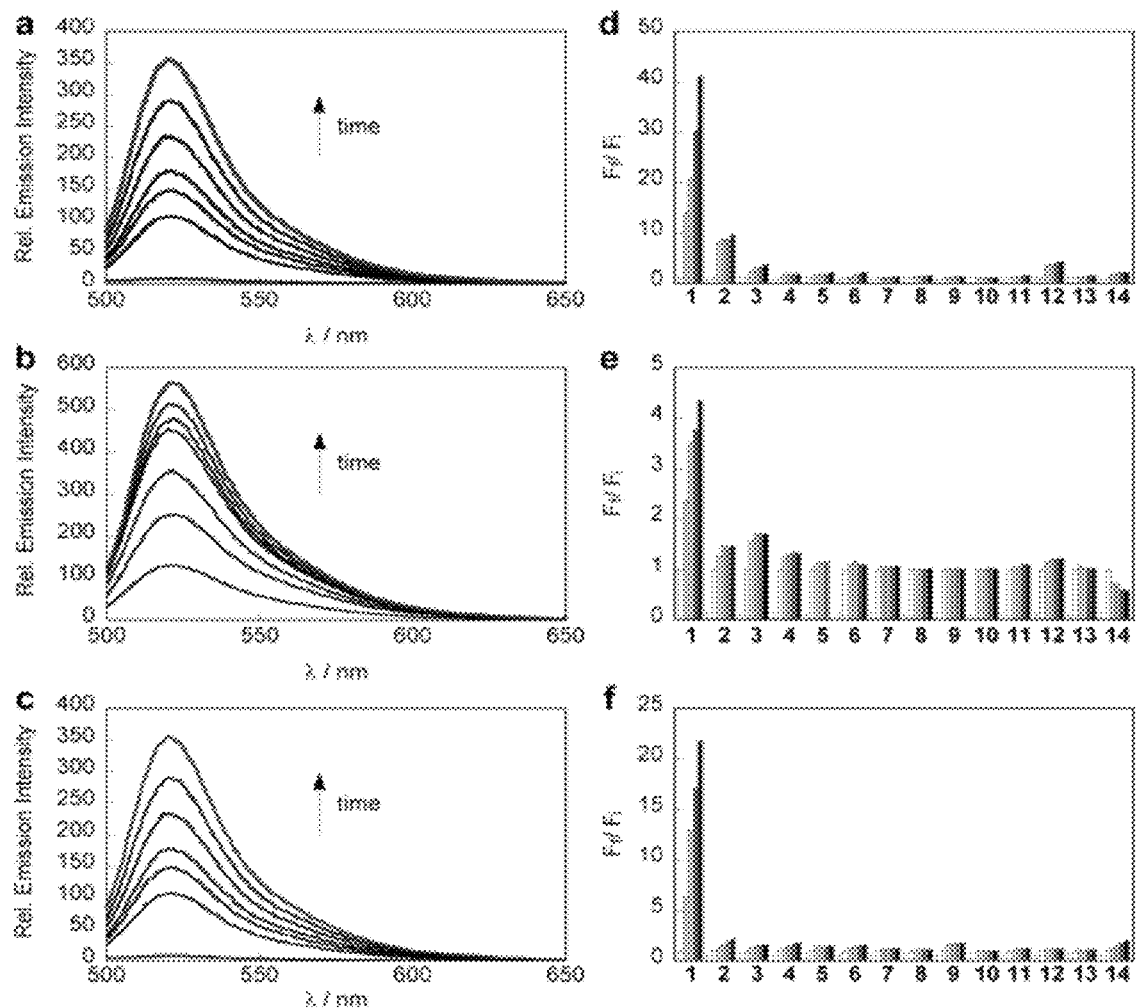
FIG. 9. Fluorescence responses of (a) 10 μM SF4 (b) 10 μM SF5 and (c) 10 μM SF7 to 100 μM H$_2$S. Data were acquired at 25° C. in 20 mM HEPES buffered to pH 7.4 with excitation at $\lambda_{ex}$=488 nm. Emission was collected between 498 and 700 nm. Time points represent 0, 10, 20, 30, 40, 50, and 60 min (red trace) after addition of 100 μM H$_2$S. Fluorescence responses of (d) 10 μM SF4 (e) 10 μM SF5 and (f) 10 μM SF7 to biologically relevant RSS, ROS, and RNS. Bars represent relative responses at 525 nm at 0, 15, 30, 45, 60 min after addition of RSS, RNS, or ROS. Data shown are for 5 mM glutathione, 500 μM cysteine, and 100 μM for other RSS, RNS, and ROS. Data were acquired in 20 mM HEPES buffered at pH 7.4 with excitation at $\lambda_{ex}$=488 nm. 1. H$_2$S; 2. glutathione; 3. cysteine; 4. lipoic acid; 5. Na$_2$SO$_3$; 6. NaS$_2$O$_3$; 7. KSCN; 8. S-nitroso glutathione; 9. NaNO$_2$; 10. NO; 11. H$_2$O$_2$; 12. O$_2^-$; 13. $^t$BuOOH; 14. HOCl.

FIG. 9(d-f). Fluorescence responses of (d) 10 μM SF4 (e) 10 μM SF5 and (f) 10 μM SF7 to biologically relevant RSS, ROS, and RNS. Bars represent relative responses at 525 nm at 0, 15, 30, 45, 60 min after addition of RSS, RNS, or ROS. Data shown are for 5 mM glutathione, 500 μM cysteine, and 100 μM for other RSS, RNS, and ROS. Data were acquired in 20 mM HEPES buffered at pH 7.4 with excitation at $\lambda_{ex}$=488 nm. 1. $H_2S$; 2. glutathione; 3. cysteine; 4. lipoic acid; 5. $Na_2SO_3$; 6. $NaS_2O_3$; 7. KSCN; 8. S-nitroso glutathione; 9. $NaNO_2$; 10. NO; 11. $H_2O_2$; 12. $O_2^-$; 13. $^tBuOOH$; 14. HOCl.

Example 2.6

Cell Culture.

Cell culture media were prepared from endothelial cell growth supplement (ECGS). Cells were passaged every 2-3 days and used between passages 4 and 17.

Example 2.7

Confocal Imaging Experiments.

Confocal fluorescence imaging studies were performed with a Zeiss laser scanning microscope 710 with a 40× water objective lens, with Zen 2009 software (Carl Zeiss). SF5-AM and SF7-AM were excited using a 488 nm Ar laser, and emission collected using a META detector between 500 and 650 nm. Hoechst 33342 was excited with a 405 nm diode laser, and emission collected using a META detector between 450 and 500 nm. The cells were imaged at 37° C. and 5% $CO_2$ throughout the course of the experiment. All imaging experiments were performed in 4-well or 8-well chamber slides. Image analysis was performed using ImageJ (National Institute of Health) or Zen 2009 software (Carl Zeiss). For trapping and exogenous $H_2S$ addition, images were quantified by using the mean pixel intensity after setting a common threshold for all images. Images were quantified by performing a maximum intensity projection in Zen 2009 software (Carl Zeiss) and using the mean pixel intensity after setting a common threshold for all images.

Example 2.8

Trapping.

HUVEC were incubated with 5 μM SF2, 5 μM SF4, 2.5 μM SF5-AM, or 2.5 μM SF7-AM for 30 min at 37° C. and 5% $CO_2$. Four different fields of cells were then imaged. The media was replaced and cells were imaged at four fields at 5, 30, and 60 minutes after media exchange.

Figure 10:
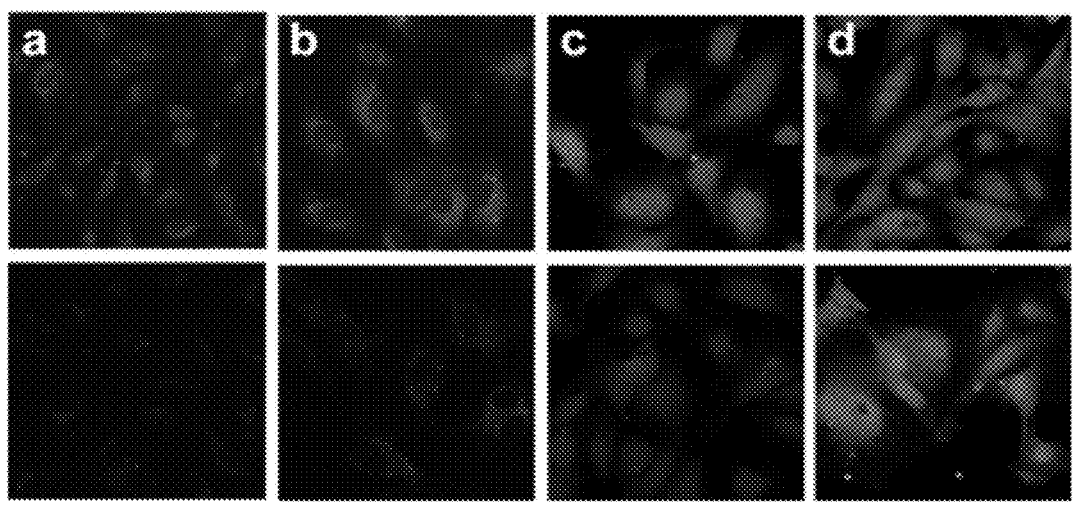
FIG. 10. Uptake and retention of SF2, SF4, SF5-AM, and SF7-AM. HUVEC were loaded with (a) 5 μM SF2 (b) 5 μM SF4 (c) 2.5 μM SF5-AM or (d) 2.5 μM SF7-AM for 30 min, then imaged before (top) and 60 min after (bottom) replacing media.

FIG. 10. Uptake and retention of SF2, SF4, SF5-AM, and SF7-AM. HUVEC were loaded with (a) 5 μM SF2 (b) 5 μM SF4 (c) 2.5 μM SF5-AM or (d) 2.5 μM SF7-AM for 30 min, then imaged before (top) and 60 min after (bottom) replacing media.

Figure 11:
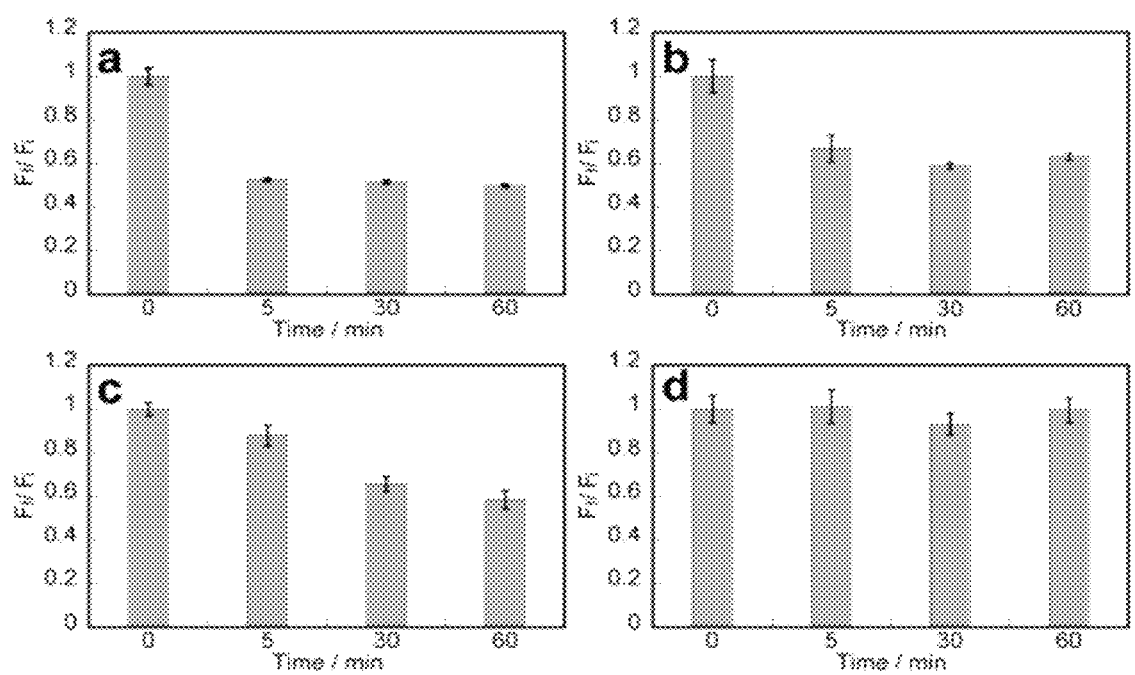
FIG. 11. Uptake and retention of SF2, SF4, SF5-AM, and SF7-AM. HUVEC were loaded with (a) 5 μM SF2 (b) 5 μM SF4 (c) 2.5 μM SF5-AM or (d) 2.5 μM SF7-AM for 30 min, then washed with ECGS media and imaged before and at 5, 30, and 60 min after dye washing.
Figure 12:
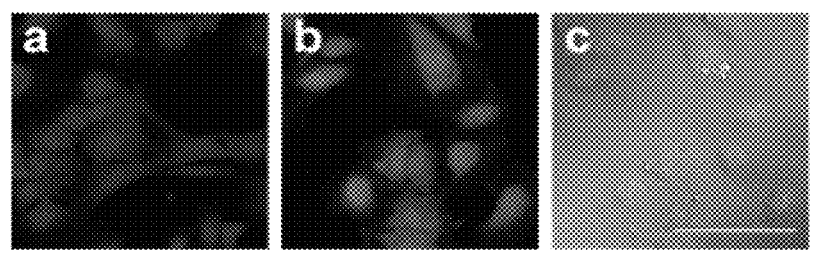
FIG. 12. Confocal images of H$_2$S detection in live HUVEC using SF7-AM. (a) HUVEC incubated with 5 μM SF7-AM for 30 min at 37° C., washed, and then treated with H$_2$O as a vehicle control for 30 min at 37° C. (b) HUVEC incubated with 5 μM SF7-AM for 30 min at 37° C., washed, and then treated with 25 μM NaSH for 30 min at 37° C. (c) Brightfield images of the same field of cells in (b) overlaid with images of 1 μM Hoescht stain at 37° C. Scale bars represent 100 μm.
Figure 13:
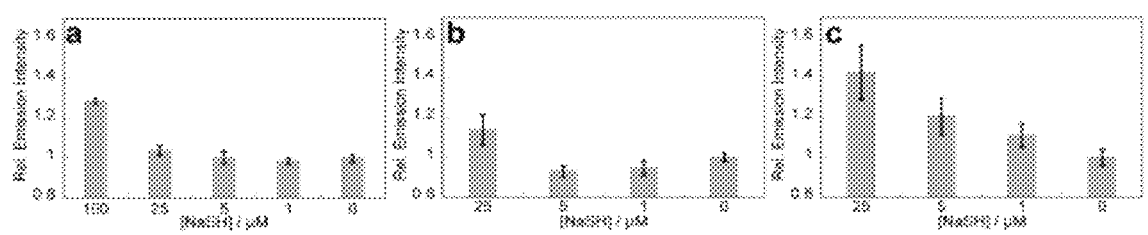
FIG. 13. Quantification of confocal images of H$_2$S detection in live HUVEC using SF7-AM. (a) HUVEC incubated with 5 μM SF4 for 30 min at 37° C., and then treated with 100, 25, 5, 1, and 0 μM NaSH for 30 min at 37° C. (b) HUVEC incubated with 5 μM SF5-AM for 30 min at 37° C., washed, and then treated with 25, 5, 1, and 0 μM NaSH for 30 min at 37° C. (c) HUVEC incubated with 5 μM SF7-AM for 30 min at 37° C., washed and then treated with 25, 5, 1, and 0 μM NaSH for 30 min at 37° C. Error bars are s.e.m.
Figure 14:
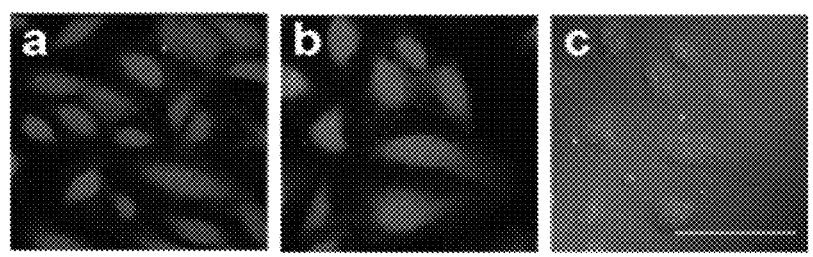
FIG. 14. Confocal images of H$_2$S detection in live HUVEC using SF5-AM. (a) HUVEC incubated with 5 μM SF5-AM for 30 min at 37° C., washed, and then treated with H$_2$O as a vehicle control for 30 min at 37° C. (b) HUVEC incubated with 5 μM SF5-AM for 30 min at 37° C., washed, and then treated with 25 μM NaSH for 30 min at 37° C. (c) Brightfield images of the same field of cells in (b) overlaid with images of 1 μM Hoescht stain at 37° C. Scale bars represent 100 μm.
Figure 15:
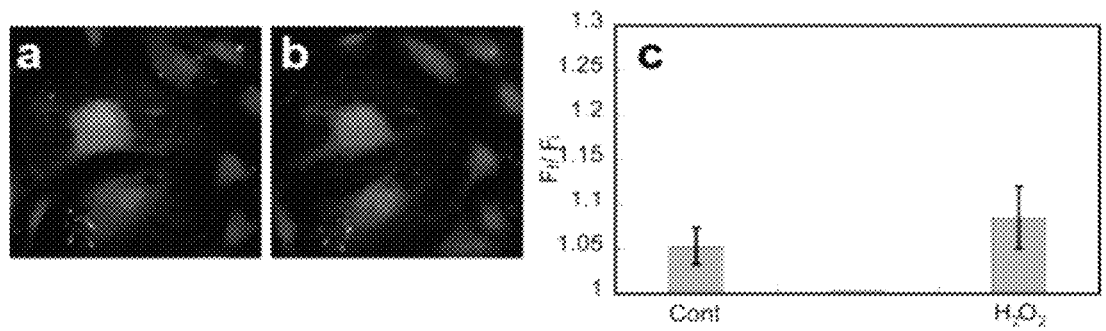
FIG. 15. (a) HUVEC incubated with 2.5 μM SF7-AM for 30 min at 37° C., washed, imaged before (a) and after (b) treatment with 100 μM H$_2$O$_2$ for 30 min at 37° C. and 5% CO$_2$. (c) Quantification of images in (a) and (b). Error bars are s.e.m.

FIG. 11. Uptake and retention of SF2, SF4, SF5-AM, and SF7-AM. HUVEC were loaded with (a) 5 μM SF2 (b) 5 μM SF4 (c) 2.5 μM SF5-AM or (d) 2.5 μM SF7-AM for 30 min, then washed with ECGS media and imaged before and at 5, 30, and 60 min after dye washing.

Example 2.9

Exogenous $H_2S$.

HUVEC were incubated with 5 μM SF4, 2.5 μM SF5-AM or 2.5 μM SF7-AM for 30 min at 37° C. and 5% $CO_2$. The media was exchanged and cells were incubated with 1, 5, and 25 μM NaSH for SF5-AM and SF7-AM, and 1, 5, 25, and 100 μM NaSH for SF4 at 37° C. and 5% $CO_2$ for 30 min. Cells were then imaged at 4 different fields.

REFERENCES

References.
(S1) Lavis, L. D.; Chao, T.-Y.; Raines, R. T. *ACS Chem. Biol.* 2006, 4, 252-260.
(S2) Prepared by an adaptation of a literature procedure: Abe, H.; Wang, J.; Furukawa, K.; Oki, K.; Uda, M.; Tsuneda, S.; Ito, Y. *Bioconjugate Chem.* 2008, 19, 1219-1226.
(S3) Williams, A. T. R.; Winfield, S. A.; Miller, J. N. *Analyst* 1983, 108, 1067-1071.
(S4) Hart, T. W. *Tetrahedron Lett.* 1985, 26, 2013-2016.

The articles "a," "an" and "the" as used herein do not exclude a plural number of the referent, unless context clearly dictates otherwise. The conjunction "or" is not mutually exclusive, unless context clearly dictates otherwise. The term "include" refers to nonexhaustive examples.

All references, publications, patent applications, issued patents, accession records, databases, websites and document URLs cited herein are incorporated by reference in their entirety for all purposes.

We claim:
1. A compound selected from:

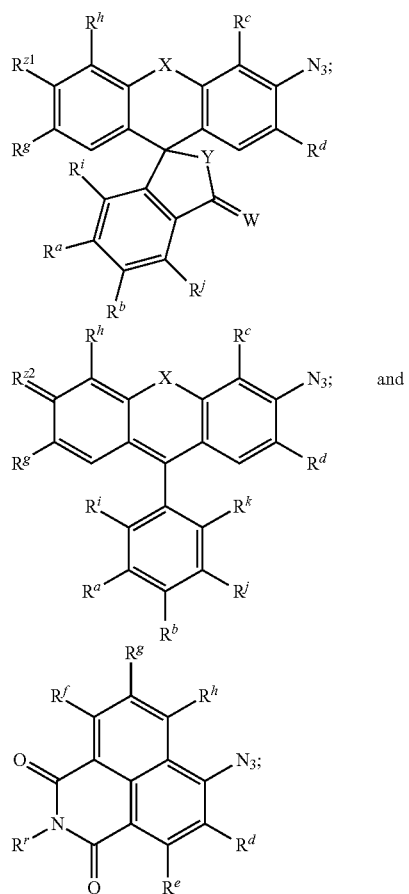

and wherein
$R^a$ and $R^b$ are independently selected from H, —C(O)OR$^4$, —C(O)NR$^5$R$^6$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, halogen, —OR$^{11}$, —SR$^{11}$, —NR$^{12}$R$^{13}$, —C(O)OR$^{11}$, —CHO, —OSO$_3$R$^{11}$, and —C(O)NR$^{12}$R$^{13}$;

wherein at least one of $R^a$ or $R^b$ is not H;

wherein $R^4$, $R^5$, $R^6$, $R^{11}$, $R^{12}$ and $R^{13}$ are independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl;

wherein $R^5$ and $R^6$ are optionally joined to form, along with the atom to which they are attached, a substituted or unsubstituted heterocycloalkyl; and $R^{12}$ and $R^{13}$ are optionally joined to form, along with the atom to which they are attached, a substituted or unsubstituted heterocycloalkyl;

$R^c$, $R^d$, $R^e$, $R^f$, $R^g$, $R^h$, $R^i$, $R^j$, and $R^k$ are independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, halogen, —OR$^{11}$, —SR$^{11}$, —NR$^{12}$R$^{13}$, —C(O)OR$^{11}$, —CHO, —OSO$_3$R$^{11}$, and —C(O)NR$^{12}$R$^{13}$;

$R^r$ is heteroalkyl substituted with OC(O)R$^{14}$, wherein R$^{14}$ is $C_1$-$C_6$ substituted or unsubstituted alkyl;

$R^{z1}$ is a member selected from —OR$^3$, —SR$^3$, —NR$^1$R$^2$, -L$^1$R$^L$, —N$_3$, —N(H)C(O)OR$^3$ and —N(H)C(O)NR$^1$R$^2$;

wherein $R^1$, $R^2$ and $R^3$ are independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl;

wherein $R^1$ and $R^2$ are optionally joined to form, along with the atom to which they are attached, a substituted or unsubstituted heterocycloalkyl;

L$^1$ is a linker which is a member selected from a bond, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl;

$R^L$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl;

$R^{z2}$ is a member selected from O, S, NR$^1$, N$^+$R$^1$R$^2$, and L$^1$R$^L$;

W is a member selected from O, NR$^7$, S, and Se;

wherein R$^7$ is a member selected from H, substituted or unsubstituted alkyl, substituted or unsubstituted heteroalkyl;

X is a member selected from O, S, Se, CR$^8$R$^9$, and SiR$^8$R$^9$;

wherein R$^8$ and R$^9$ are independently selected from H, substituted or unsubstituted alkyl, substituted or unsubstituted heteroalkyl;

Y is a member selected from O, NR$^{10}$, S, and Se;

wherein R$^{10}$ is a member selected from H, substituted or unsubstituted alkyl, substituted or unsubstituted heteroalkyl.

2. The compound according to claim 1, selected from:

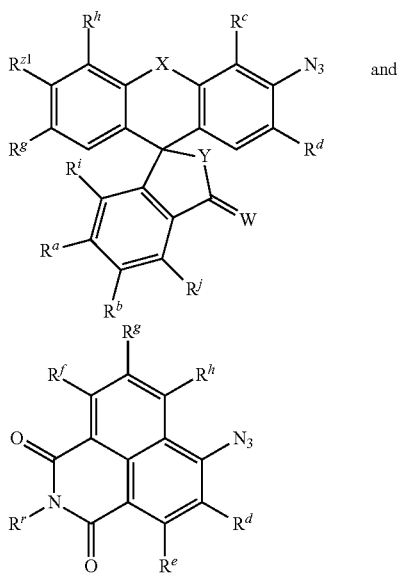

wherein
R$^c$, R$^d$, R$^e$, R$^f$, R$^g$, R$^h$, R$^i$, and R$^j$ are each H; and
W, X and Y are each O.

3. The compound according to claim 2, wherein
R$^a$ and R$^b$ are independently selected from H, —C(O)OR$^4$, and —C(O)NR$^5$R$^6$, wherein at least one of R$^a$ or R$^b$ is not H; and
R$^{z1}$ is a member selected from —NR$^1$R$^2$, —N$_3$, —N(H)C(O)OR$^3$ and —N(H)C(O)NR$^1$R$^2$.

4. The compound according to claim 3, selected from:

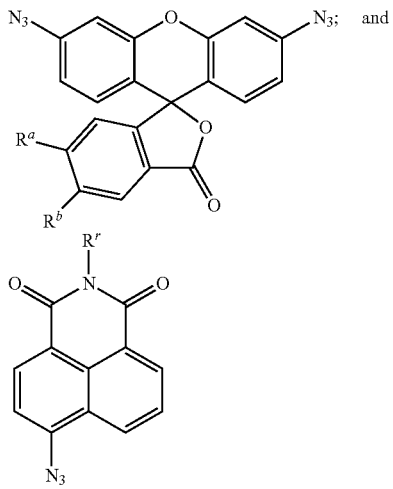

wherein
R$^{z1}$ is a member selected from —N(H)C(O)OR$^3$ and —N(H)C(O)NR$^1$R$^2$;
R$^a$ and R$^b$ are independently selected from H, —C(O)OR$^4$ and —C(O)NR$^5$R$^6$, wherein at least one of R$^a$ or R$^b$ is not H; and
R$^r$ is heteroalkyl substituted with —OC(O)R$^{14}$, wherein R$^{14}$ is a member selected from unsubstituted C$_1$, C$_2$, C$_3$, C$_4$, C$_5$ or C$_6$ alkyl.

5. The compound according to claim 4, wherein R$^a$ is H.

6. The compound according to claim 4, wherein R$^5$ and R$^6$ are alkyl substituted with —C(O)OR$^4$.

7. The compound according to claim 4, selected from:

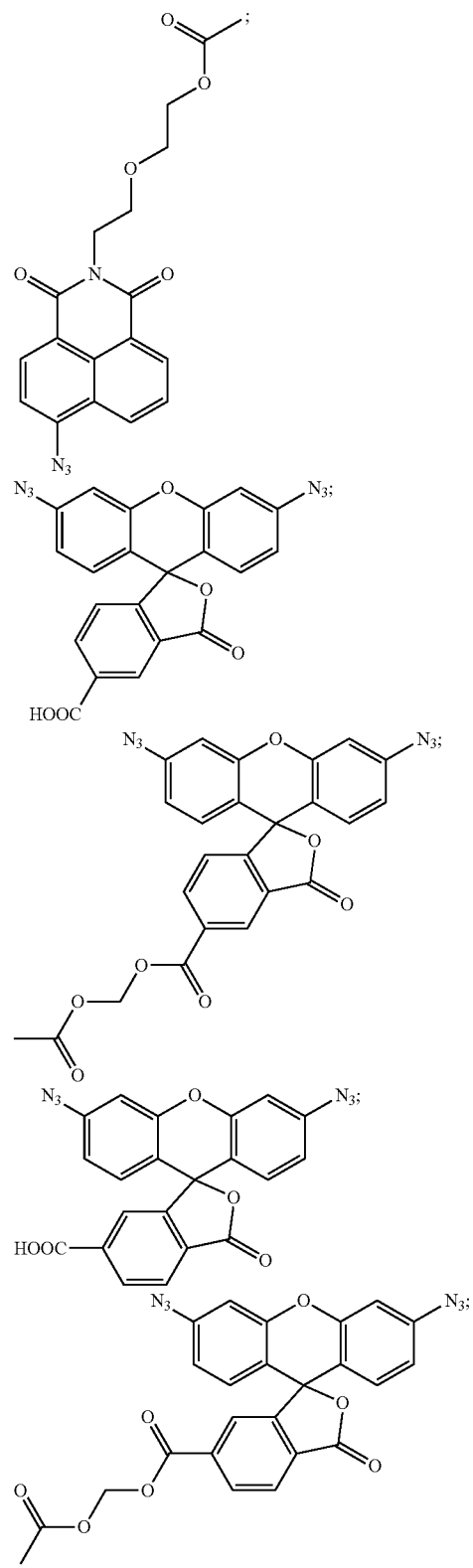

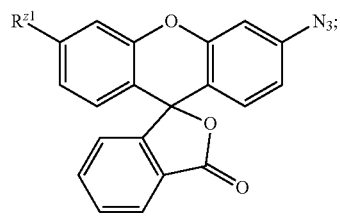

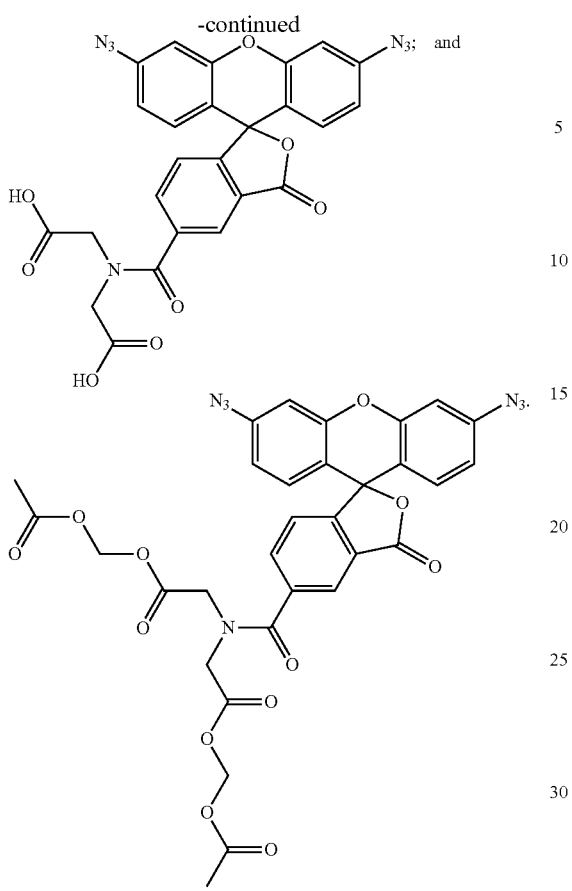

8. The compound according to claim 1, wherein said compound is a probe for a reactive sulfur species; wherein the azide moiety undergoes a reduction upon contact with the reactive sulfur species, forming a reaction product, thereby generating a detectable signal.

9. The compound according to claim 8, wherein said reactive sulfur species is $H_2S$.

10. An assay mixture comprising a compound according to claim 1; and a suitable solvent for the compound.

11. A method of detecting a reactive sulfur species in a sample comprising:
(a) contacting the sample with the probe according to claim 8; and
(b) detecting the reaction product emitting the detectable signal.

12. The method according to claim 11, wherein said reactive sulfur species is $H_2S$.

13. The method according to claim 11, wherein said sample comprises a cell, and the reaction product is formed within said cell.

14. The method according to claim 13, wherein said cell is a living cell.

15. The method according to claim 11, wherein said reaction product is detected in real-time.

16. A compound of the structure:

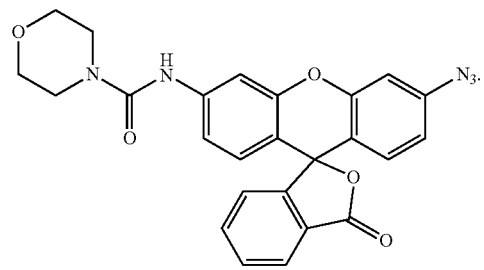

wherein
$R^{z1}$ is a member select from —N(H)C(O)OR$^3$ and —N(H)C(O)NR$^1$R$^2$
wherein R$^1$ and R$^2$ are independently selected from H, substituted or
unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl and R$^1$ and R$^{2'}$ together with the atom to which they are attached are optionally joined to form a substituted or unsubstituted heterocycloalkyl ring; and
wherein R$^3$ is independently selected from H, substituted alkyl, substituted or
unsubstituted heteroalkyl, substituted or unsubstituted cycloalkyl, substituted or unsubstituted heterocycloalkyl, substituted or unsubstituted aryl and substituted or unsubstituted heteroaryl.

17. The compound according to claim 16 which is:

* * * * *